United States Patent [19]
Meade et al.

[11] Patent Number: 6,008,190
[45] Date of Patent: Dec. 28, 1999

[54] COBALT SCHIFF BASE COMPOUNDS

[75] Inventors: Thomas J. Meade, Altadena; Toshihiko Takeuchi, San Francisco; Harry B. Gray, Pasadena; Melvin Simon, San Marino; Angelique Y. Louie, Pasadena, all of Calif.

[73] Assignee: California Institute of Technology, Pasadena, Calif.

[21] Appl. No.: 08/570,761

[22] Filed: Dec. 12, 1995

Related U.S. Application Data

[63] Continuation-in-part of application No. 08/358,068, Dec. 15, 1994.
[51] Int. Cl.$^6$ .................. A61K 31/295; A61K 31/70; A61K 38/02; C12N 9/99
[52] U.S. Cl. .................. 514/6; 424/DIG. 6; 435/184; 514/44; 514/501; 530/345; 530/400; 536/23.1; 556/32; 556/138; 556/146
[58] Field of Search .................. 424/1.65, 1.69, 424/1.73, 646, DIG. 6; 435/214, 184; 514/6, 23, 44, 129, 501; 530/345, 400, 409; 536/23.1, 121; 556/13, 32, 138, 146

[56] References Cited

U.S. PATENT DOCUMENTS

| | | | |
|---|---|---|---|
| 4,451,270 | 5/1984 | Roman | 55/38 |
| 4,514,522 | 4/1985 | Sievers et al. | 521/53 |
| 4,735,634 | 4/1988 | Norman et al. | 55/16 |
| 4,866,053 | 9/1989 | Dori et al. | 514/184 |
| 4,866,054 | 9/1989 | Dori et al. | 154/184 |
| 4,948,506 | 8/1990 | Lonsdale et al. | 210/490 |
| 5,049,557 | 9/1991 | Dori et al. | 514/185 |
| 5,106,841 | 4/1992 | Scheer | 514/185 |
| 5,142,076 | 8/1992 | Dori et al. | 556/146 |
| 5,210,096 | 5/1993 | Scheer | 514/501 |
| 5,324,879 | 6/1994 | Hawthorne | 585/511 |
| 5,880,149 | 3/1999 | Grinstaff et al. | 514/492 |

FOREIGN PATENT DOCUMENTS

96/18402  6/1996  WIPO.

OTHER PUBLICATIONS

Marcu et al., "New Cobalt Chelates with Ethylenediimino–Bis–Benzoylacetone," *Revue Roumaine de Chimie*, 34(4):1029–1035 (1989).

El Absy et al., "Spectrophotometric and Derivatographic Study on Some new Tetradentate Mixed Chelates of Cobalt (III) With Acetylacetone Derivatives," *Revue Roumaine de Chimie*, 27(8):917–925 (1982).

Ranford et al., "Cytotoxicity and Antiviral Activity of Transition–Metal Salicylato Complexes and Crystal Structure of Bis (Diisopropylsalicylato) (1,10–Phenanthroline) Copper (II)," *J. Chem. Soc. Dalton Trans.*, 3393–3399 (1993).

(List continued on next page.)

*Primary Examiner*—Jeffrey E. Russel
*Attorney, Agent, or Firm*—Flehr Hohbach Test Albritton & Herbert LLP; Richard F. Trecartin, Esq.; Robin M. Silva, Esq.

[57] ABSTRACT

The invention relates to novel cobalt compounds, having a general structure

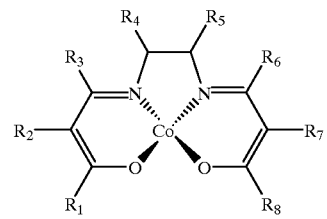

wherein Co is either Co(II) or Co(III), and each of the R groups is selected from the group consisting of hydrogen, alkyl, hydrophilic organic acid, alkyl amine, amine, alkyl alcohol, alcohol, polypeptide or nucleic acid. The invention further relates to methods of using such compounds to reduce the biological activity of proteins, particularly enzymes and zinc finger-containing proteins.

21 Claims, 6 Drawing Sheets

OTHER PUBLICATIONS

Fujii et al., "Preparation and Properties of Cobalt (III)–Schiff Base Complexes Containing Optically Active Ligands at the Axial Sites," *Chemical Abstracts*, 83(2):Abstract No. 21107u (Jul. 1975).

Ware et al., "Hypoxia–Selective Antitumor Agents. 7. Metal Complexes of Aliphatic Mustards as a New Class of Hypoxia–Selective Cytotoxins. Synthesis and Evaluation of Cobalt (III) Complexes of Bidentate Mustards," *J. Med. Chem.*, 36:1839–1846 (1993).

Berg, J.M., "Zinc–Finger Proteins," *Current Opinion in Structural Biology*, 3:11–16 (1993).

Dannull et al., "Specific Binding of HIV–1 Nucleocapsid Protein to PSI RNA In vitro Requires N–Terminal Zinc Finger and Flanking Basic Amino Acid Residues," *The Embo Journal*, 13(7):1525–1533 (1944).

Sakaguchi et al., "Identification of a Binding Site of the Human Immunodeficiency Virus Type 1 Nucleocapsid Protein," *Proc. Natl. Acad. Sci. USA*, 90:5219–5223 (1993).

Berg, J.M., "Zinc Finger Domains: From Predictions to Design," *Acc. Chem. Res.*, 28:14–19 (1995).

Berg, J.M., "Zinc Finger Domains: Hypotheses and Current Knowledge," *Annu. Rev. Biophys. Biophys. Chem.*, 19:405–451 (1990).

Kaptein, R., "Protein–Nucleic Acid Interactions by NMR," *Current Opinion in Structural Biology*, 3:50–56 (1993).

Berg, J.M., "SP1 and the Subfamily of Zinc Finger Proteins with Guanine–Rich Binding Sites," *Proc. Natl. Acad. Sci. USA*, 89:11109–11110 (1992).

Evans, R.M., "The Steroid and Tyroid Hormone Receptor Superfamily," *Science*, 240:889–895 (1988).

Freedman et al., "The Function and Structure of the Metal Coordination Sites Within the Glucocorticoid Receptor DNA Binding Domain," *Nature*, 334:543–546 (1988).

Berg, J.M., "Potential Metal–Binding Domains in Nucleic Acid Binding Proteins," *Science*, 232:485–487 (1986).

Evans et al., "Zinc Fingers: Gilt By Association," *Cell*, 52:1–3 (1988).

Berg, J.M., "DNA Binding Specificity of Steroid Receptors," *Cell*, 57:1065–1068 (1989).

Beato, M., "Gene Regulation by Steroid Hormones," *Cell*, 56:335–344 (1989).

Berg, J.M., "Metal–Binding Domains in Nucleic Acid–Binding and Gene–Regulatory Proteins," *Prog. Inorg. Chem.*, 37:143–184 (1989).

Bhattacharya et al., "Ambient Oxygen Activating Water Soluble Cobalt–Salen Complex for DNA Cleavage," *J. Chem. Soc., Commun.*, 24:2489–2490 (1995).

Spiratos et al., "Coordination Polymers. VI. Preparation adn Characterization of Some Azomethine Chelate Polymers," *Chem. Abstr.*, 101(26):7 (abstract no. 231134s) (1984).

Reisenhofer et al., "Effect of Solvents on Electrode Processes of Cobalt Schiff Base Complexes and their Organometallic Derivatives," *Chem. Abstracts*, 95(8):20 (Abstract No. 469873 (1981).

Fujii, Preparation and Properties of Cobalt(III)–Schiff–Base . . . J.Sci. Hiroshima Univ., Ser. A. Aug.–Dec. 1974, vol. 38, Nos. 2–3, pp. 313–326.

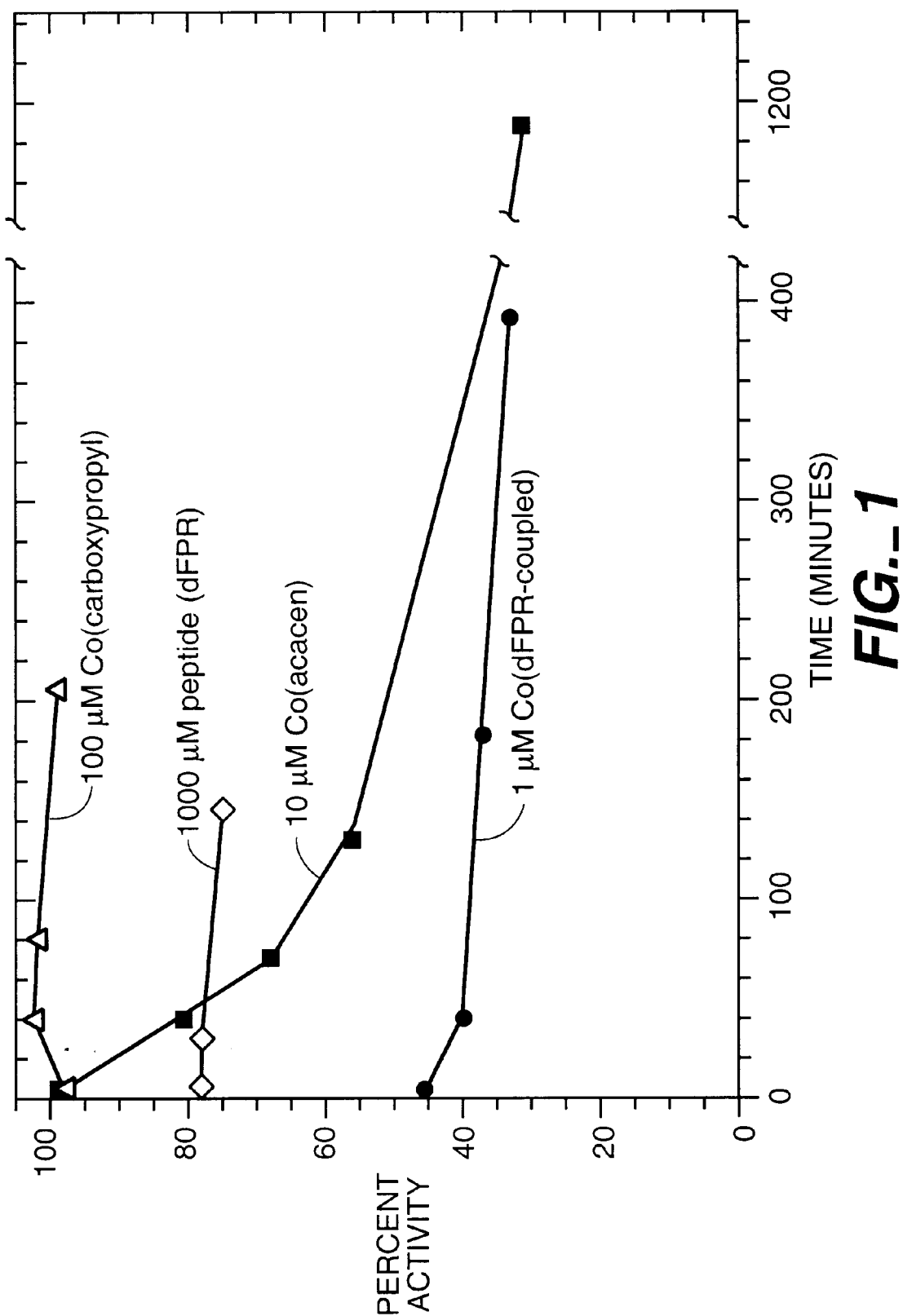
FIG._1

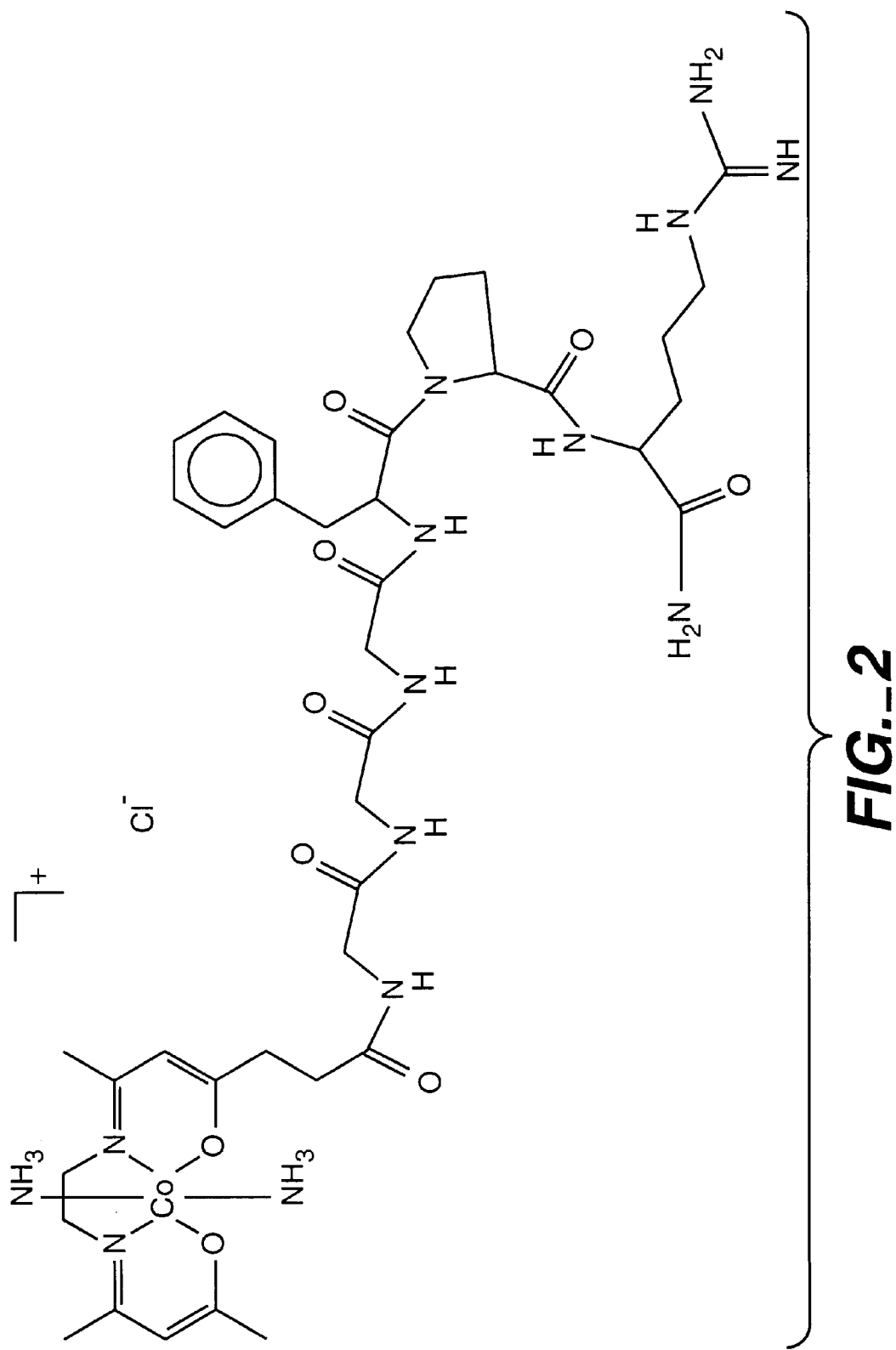
FIG._2

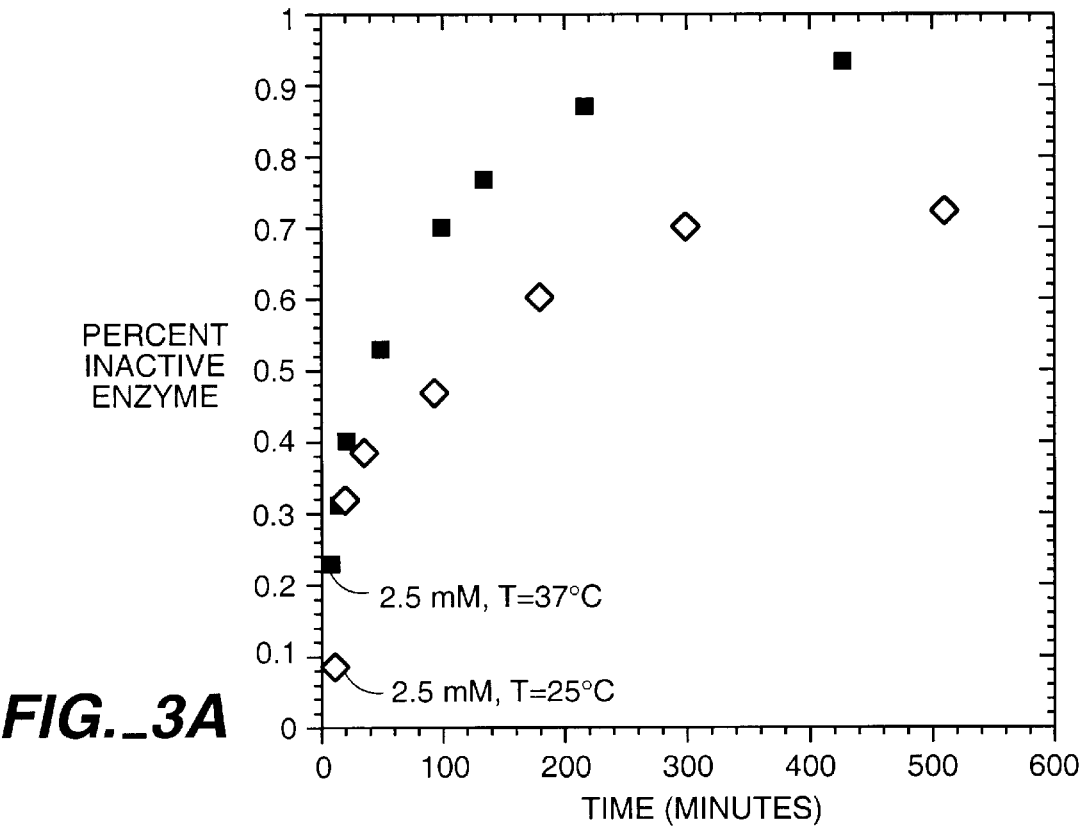
FIG._3A
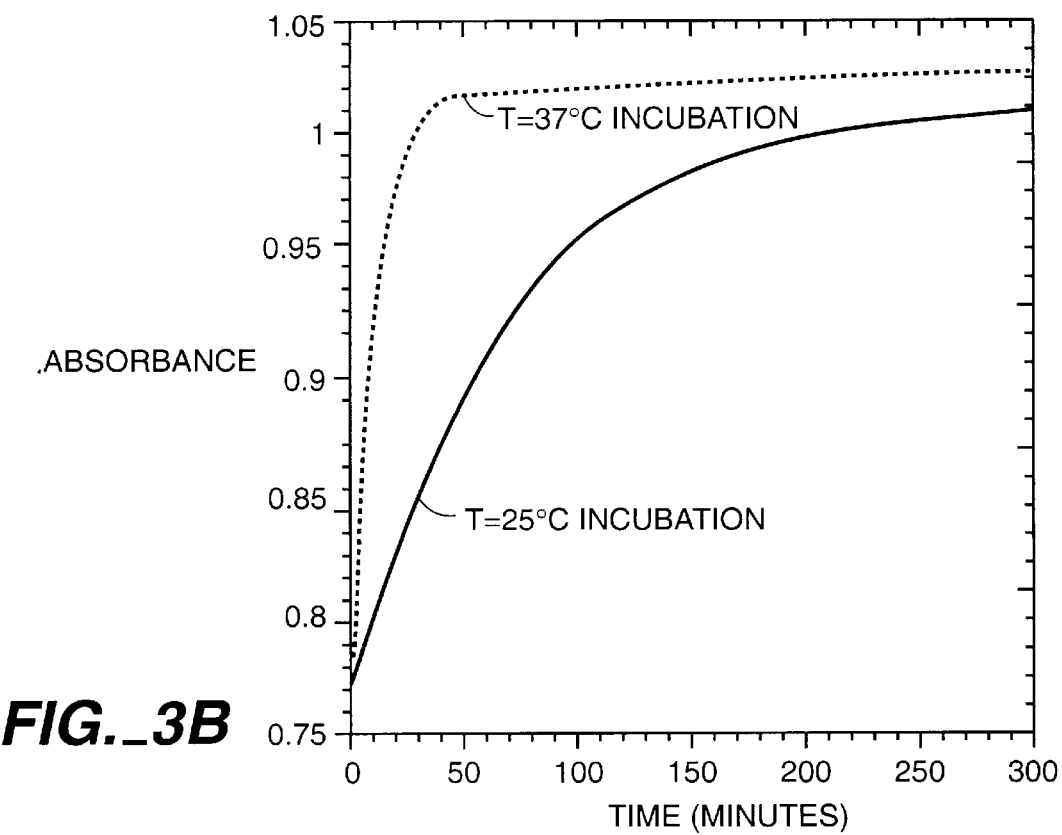
FIG._3B

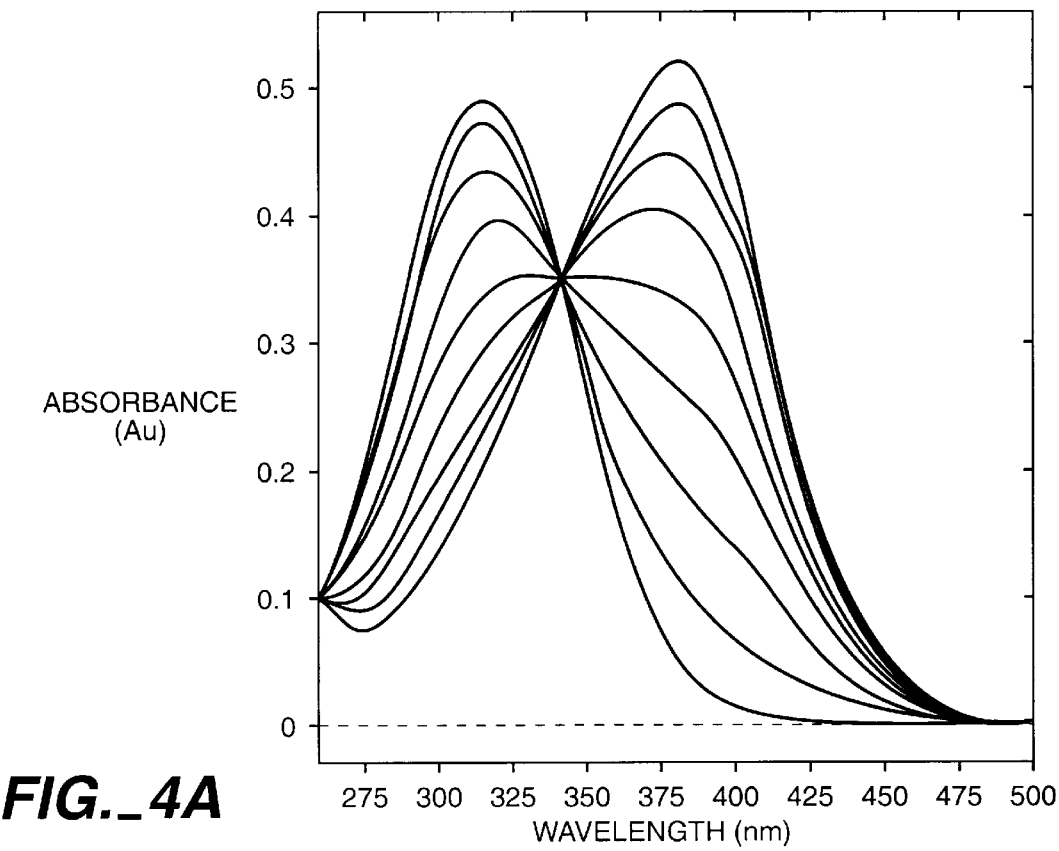
FIG._4A
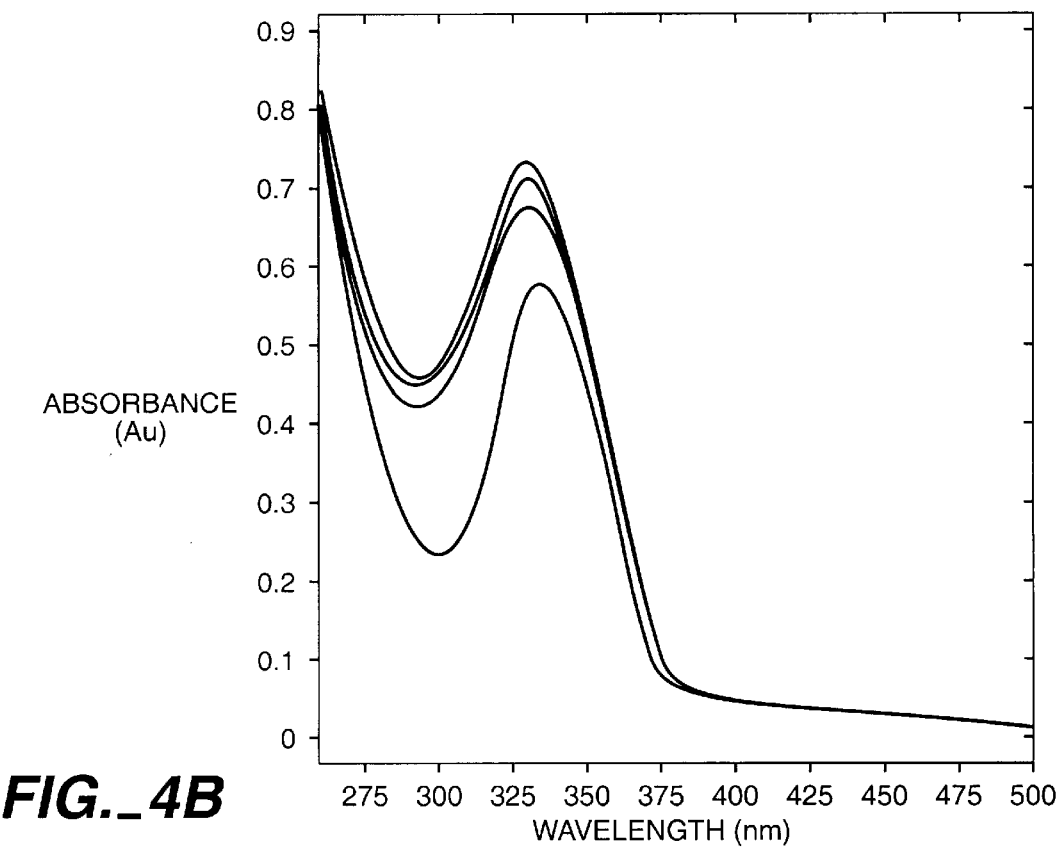
FIG._4B

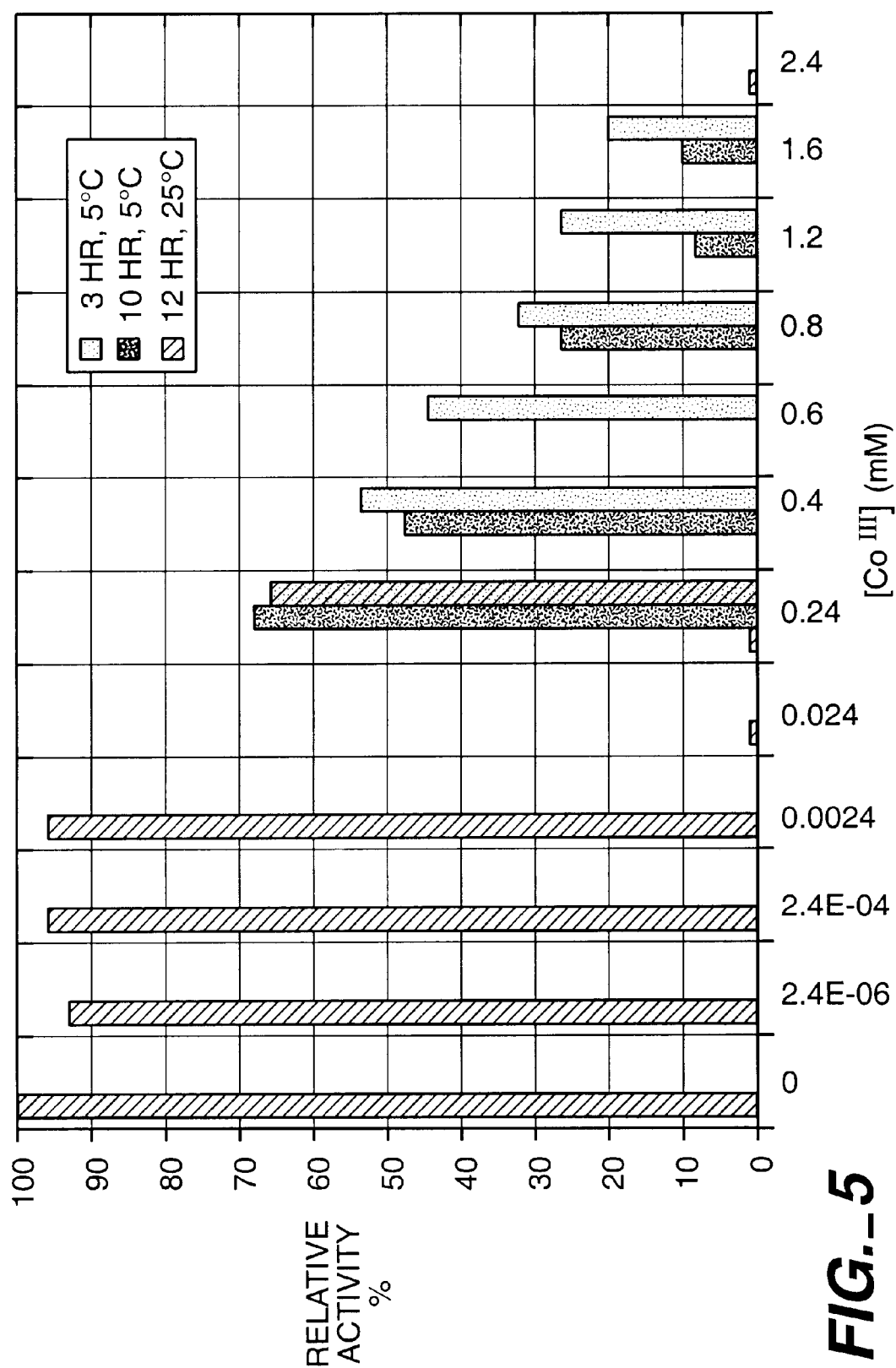
FIG._5

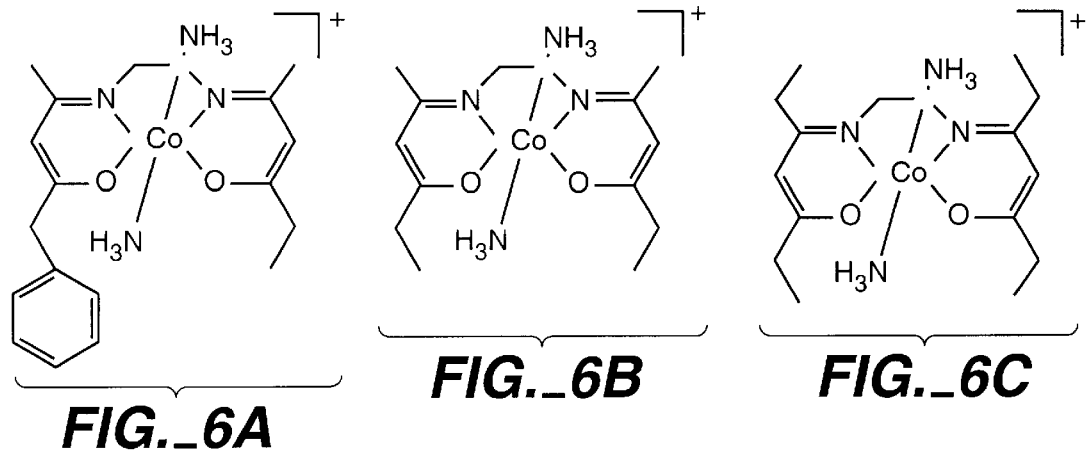
FIG._6A  FIG._6B  FIG._6C
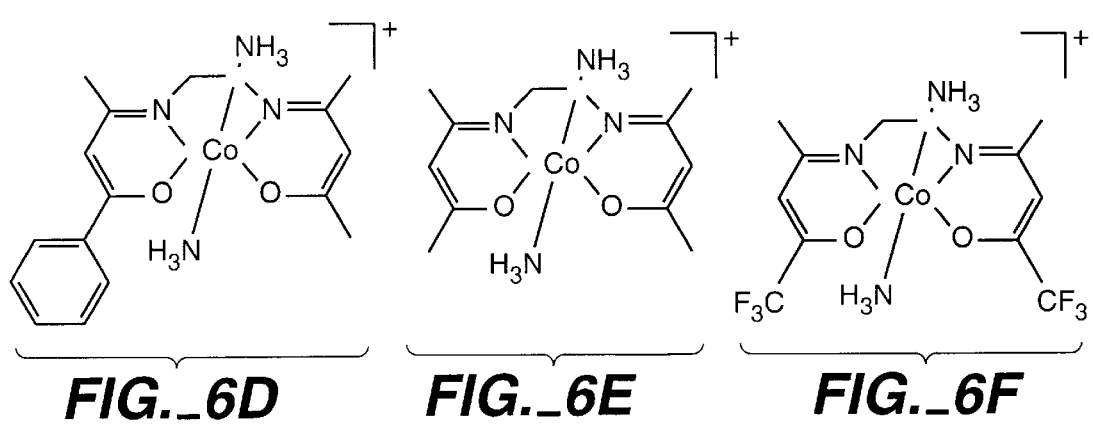
FIG._6D  FIG._6E  FIG._6F
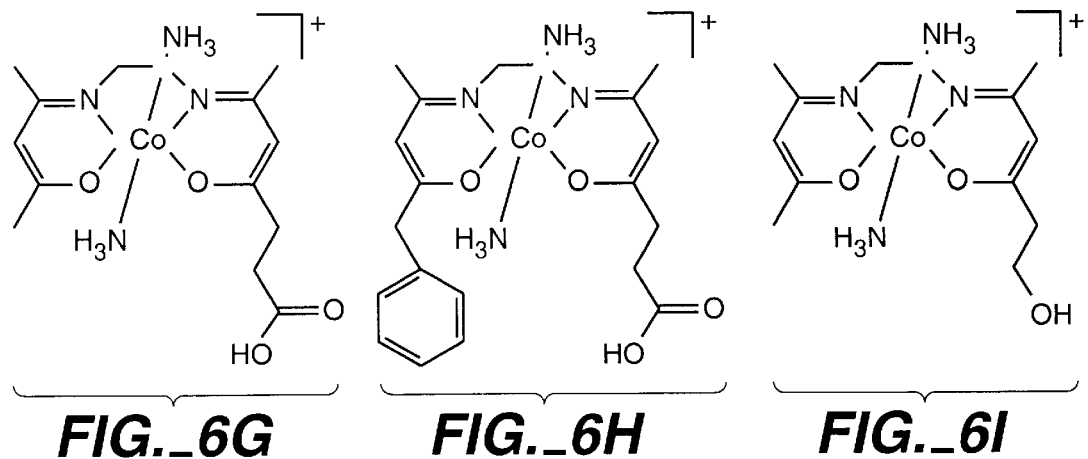
FIG._6G  FIG._6H  FIG._6I

COBALT SCHIFF BASE COMPOUNDS

This is a continuation-in-part application of U.S. Ser. No. 08/358,068, filed Dec. 15, 1994.

FIELD OF THE INVENTION

The invention relates to cobalt compounds and methods of using such compounds to reduce the biological activity of proteins.

BACKGROUND OF THE INVENTION

The use of metals in medicine has grown impressively in recent years as the result of a greatly advancing understanding of the structures of biologically active metal complexes and metal-containing proteins.

Currently, a class of cobalt-containing, complexes, where the cobalt is Co(III), has been shown to have antiviral, antitumor and antimicrobial activities, as well as showing use in the treatment of inflammation and burns (see U.S. Pat. Nos. 4,866,054, 4,866,053, 5,049,557, 5,106,841, 5,142,076, and 5,210,096, and Wooley et al., Agents and Actions 35:274 (1992)). These complexes have a basic core structure shown below:

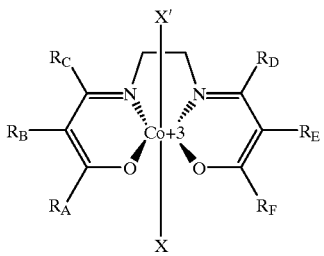

These complexes are hypothesized to be active-oxygen or superoxide antagonists, thus suppressing medical conditions associated with free radicals such as inflammation.

Additionally a Co(II) complex of isopropyl salicylic acid has been made and reported to be cytotoxic. (Ranford et al.. *J. Chem. Soc. Dalton Trans.* (1993) 3393).

Finally the oxidation of certain Co(III) complexes containing coordinated nitrogen mustards causes the release of activated aliphatic mustards which can act as diffusible cytotoxins. (Ware et al.. *J. Med. Chem.* 36:1839 (1993)).

SUMMARY OF THE INVENTION

It is an object of the invention to provide novel cobalt compounds, including cobalt compounds containing polypeptides and nucleic acids. It is a further object to provide methods for the inhibition of proteins, such as enzymes, using these cobalt complexes.

In accordance with these objects, compositions are provided comprising water soluble tetradentate Schiff's base complexes of Co(II).

Further provided are compounds having the structure comprising Formula 1:

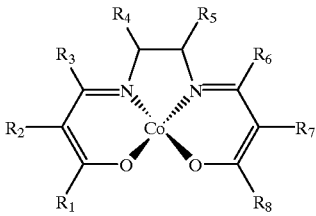

Formula 1

In Formula 1, Co is either Co(II) or Co(III), and each of $R_1$, $R_2$, $R_3$, $R_4$, $R_5$, $R_6$, $R_7$ and $R_8$ is a hydrogen, an alkyl group, an aryl group, a hydrophilic organic acid, an alkyl alcohol, an alcohol, an alkyl amine group, an amine group, a polypeptide or a nucleic acid.

Also provided are compounds of Formula 1 wherein $R_1$, $R_2$, $R_3$ and $R_4$ are each hydrogen, alkyl, or aryl.

Also provided are protein-cobalt compound complexes comprising a protein attached to the cobalt compound of Formula 1.

Further provided are methods of inhibiting a selected protein comprising contacting the selected protein with the compound of Formula 1.

Additionally provided are methods of inhibiting zinc finger proteins comprising( contacting a zinc finger protein with the cobalt compounds described herein.

BRIEF DESCRIPTION OF THE DRAWINGS

FIG. 1 depicts the inhibition of thrombin. $3.07 \times 10^{-9}$ M thrombin at 25C was assayed using Spectrozyme TH (American Diagnostics), and the reaction followed at 406 nm using a Hewlett Packard HP8452A diode array spectrophotometer with temperature control. All assays were performed in 10 mM Tris, 10 mM HEPES, 0.1% polyethylene glycol, 0.5 M NaCl, pH 7.8. The Co(III) carboxypropyl $(NH_3)_2$ (labeled as Co(carboxypropyl)) was coupled to the active site directed peptide $NH_2$-GGGdFPR-CO-NIH SEQ ID NO: 1 (labeled as peptide dFPR). The observed inhibition greatly exceeded Co(carboxypropyl)$(NH_3)$ $)_2$, the peptide, and Co(III)acacen$(NH_3)_2$ Cl (labeled as Co(acacen)). This demonstrates the principle that coupling known inhibitors to the cobalt compound can greatly increase the potency of enzyme inhibition compared with the inhibitory activity of the uncoupled components.

FIG. 2 depicts the structure of the Co(III)(acacen-GGGFPR)$(NH_3)_2$ SEQ ID NO. 2.

FIGS. 3A and 3B shows the temperature dependence of the enzyme inhibition rate correlates to the ligand exchange rate. (A): temperature dependence (see Example 3). (B): ligand exchange rate (see Example 3).

FIGS. 4A and 4B shows the inhibition of thrombin by [CoIII(acacen)$(NH_3)_2$]Cl. Thrombin was incubated for 12 hours at room temperature with (A) 0 M Co(III) and B) 2.5 mM Co(III). Spectra were taken every 30 seconds for 30 minutes to monitor the release of p-nitroaniline by enzymatic hydrolysis of a commercial substrate.

FIG. 5 shows that inhibition of thrombin is dependent on the concentration of the inhibitors the length of incubation, and the temperature of incubation.

FIGS. 6A, 6B, 6C, 6D, 6E, 6F, 6G, 6H and 6I depict the structures of cobalt compounds of the invention that have been made. Unless noted, all of the compounds are Co(III).

DETAILED DESCRIPTION OF THE INVENTION

As is described below, the present invention is directed to cobalt compounds that can exchange or bind functional moieties such as histidine on a protein's surface resulting in the inactivation of a biological activity of the protein due to the complexing of the functional moiety to the cobalt compound.

The cobalt compounds of the invention utilize either Co(II) (also depicted herein as Co+2) or Co(III) (also depicted herein as Co+3). Generally, Co(II) compounds have up to four coordination atoms, and may contain a first axial ligand, although it is possible that water molecules may be weakly associated in one or both axial ligand positions. Similarly, Co(III) compounds have up to six coordination atoms of which two are defined herein as axial ligand positions. By "axial ligand" herein is meant a ligand $L_1$ or L2 located at either the fifth or sixth coordination sites, generally depicted in the structure below:

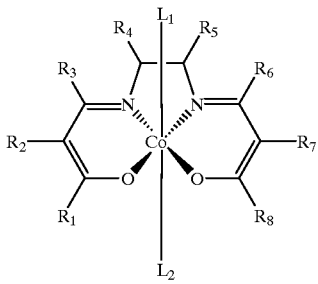

Without being bound by theory, the cobalt compounds of the invention derive their biological activity by the substitution or addition of ligands in the axial positions. The biological activity of the cobalt compounds of the invention results from the binding of a new axial ligand, most preferably the nitrogen atom of imidazole of the side chain of histidine. Presumably the amino acid serving as a new axial ligand of the cobalt compound is required by the target protein for its biological activity. Thus, as is more fully described below, proteins such as enzymes that utilize a histidine in the active site, or proteins that use histidine, for example, to bind essential metal ions, can be inactivated by the binding of the histidine in an axial ligand position of the cobalt compound, thus preventing the histidine from participating in its normal biological function.

When the cobalt is Co(III), the Co(III) complex is synthesized or formulated With two particular axial ligands, and then when the complex is added to a protein, for example, the original axial ligand or ligands are replaced by one or more ligands from a protein. This will occur either when the affinity of the protein axial ligand is higher for the cobalt compound as compared to the original axial ligand, or when the new axial ligand is present in elevated concentrations such that the equilibrium of axial ligand binding favors the binding of the new axial ligand from the protein. Thus, Co(III) complexes are made with axial ligands that can be substituted with other ligands.

Without being bound by theory, when the cobalt is Co(II), such complexes may, under certain circumstances, have a first axial ligand. The Co(II) compounds of the invention are preferably synthesized with no axial ligands. Upon incubation with a protein, certain moieties, such as the nitrogen atom of the imidazole of the side chain of histidine, within the protein can become an axial ligand, resulting in a tightly-bound protein-cobalt compound complex. This occurs when the Co(II) compound, with its four coordinating atoms from the Schiff's base, binds an imidazole moiety, for example, and is oxidized to a Co(III) compound. In one sense, this may be considered a redox reaction, since the Co(II) compound is oxidized to a Co(III) compound upon binding to the protein. Thus, the imidazole axial ligand serves as a fifth coordinating atom, and is tightly bound.

In a preferred embodiment, the nitrogen atom of an imidazole side chain of the amino acid residue histidine, contained within a target protein, is the new axial ligand. While the examples and disclosure herein particularly describe this histidine embodiment any "cobalt-reactive amino acid" may serve as the new axial ligand. A "cobalt-reactive amino acid" is one which is capable of binding to the cobalt compounds of the invention as an axial ligand. Thus, while the nitrogen of the imidazole side chain of histidine is particularly preferred, alternative embodiments utilize the nitrogen atom of the aromatic indole side chain of tryptophan, the sulfur atoms of the side chains of cysteine and methionine, the amino groups of arginine, lysine, asparagine or glutamine as the moieties which may become axial ligands as outlined above. The availability of these moieties may depend on the pH of the solution containing the protein or enzymes since in the protonated state many of these moieties are not good electron donors suitable as axial ligands.

The present invention provides cobalt compounds that may be complexed with a protein containing a suitable new axial ligand.

In one embodiment, the present invention provides water-soluble tetradentate Schiff's base compounds of Co(II).

By the term "tetradentate" herein is meant that the Schiff's base compound, which is a ligand for the Co(II), has four coordinating atoms. In a preferred embodiment, there are two nitrogen atoms and two oxygen atoms which serve as the coordinating atoms.

By the term "Schiff's base" herein is meant a substituted imine. The substituent groups are outlined below. Schiff's bases are generally the condensation products of amines and aliphatic aldehydes forming azomethines substituted on the nitrogen atom.

By the term "cobalt compound" herein is meant a tetradentate Schiff's base with a bound cobalt atom. The Schiff's base may be substituted or unsubstituted, and the cobalt may be Co(II) or Co(III).

In a preferred embodiment, the cobalt compounds have the structure depicted in Formula 1:

Formula 1

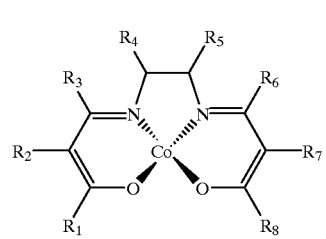

In this embodiment, Co is either Co(II) or Co(III). Each of $R_1$, $R_2$, $R_3$, $R_4$, $R_5$, $R_6$, $R_7$ and $R_8$ is a hydrogen, an alkyl group, an aryl group, a hydrophilic organic acid, an alkyl alcohol, an alcohol, an alkyl amine group, an amine group, a polypeptide or a nucleic acid. When Co is Co(II), at least one of $R_1$ through $R_8$ is hydrophilic such that the compound is soluble in aqueous solution. When Co is Co(III). at least one of $R_1$ through $R_8$ is either a polypeptide or nucleic acid.

By "alkyl" or "alkyl group" or (grammatical equivalents herein is meant a straight or branched chain alkyl group, with straight chain alkyl groups being preferred. If branched, it may be branched at one or more positions, and unless specified, at any position. Also included within the definition of an alkyl group are cycloalkyl groups such as C5 and C6 rings. In some cases, two R groups may be part of a ring structure, that is, they may be linked to form a cyclic structure.

The alkyl group may range from about 1 to 20 carbon atoms (C1–C20), with a preferred embodiment utilizing from about I to about 10 carbon atoms (C1–C10), with about C1 through about C5 being preferred. However, in some embodiments, the alkyl group may be larger, particularly if it is a straight chain alkyl. Particularly preferred is methyl.

By "aryl" or "aryl group" herein is meant aromatic rings including phenyl, benzyl, and naphthyl, heterocyclic aromatic rings such as pyridine, furan, thiophene, pyrrole, indole and purine, and heterocyclic rings with nitrogen, oxygen, sulfur or phosphorus.

The alkyl and aryl groups may be substituted, for example, a phenyl group may be a substituted phenyl group. Suitable substitution groups include, but are not limited to, alkyl and aryl groups, halogens such as chlorine, bromine and fluorine, amines, carboxyl acids, and nitro groups.

By "hydrophilic organic acid" or grammatical equivalents herein is meant an alkyl group containing one or more carboxyl groups, —COOH, i.e. a carboxyl acid. As defined above, the alkyl group may be substituted or unsubstituted. C1–C20 alkyl groups may be used with at least one carboxyl group attached to any one of the alkyl carbons, with C1–C5 being preferred. In a preferred embodiment, the carboxyl group is attached to the terminal carbon of the alkyl group. Other preferred hydrophilic organic acids include phosphonates and sulfonates. A preferred hydrophilic organic acid is propionic acid.

In a preferred embodiment, only one of the R groups is a hydrophilic organic acid, since, in the case of Co(III), this may result in a compound that is neutrally charged, and thus may cross the blood-brain barrier. Particularly preferred is the structure depicted in Formula 2:

Formula 2

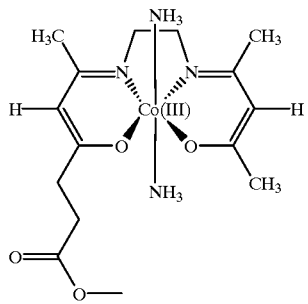

In addition the length of the alkyl group shown in Formula 2 may be altered either to encourage or prevent the carboxylic acid from "swinging around" to become an axial ligand.

By the term "amine" herein is meant an —NRR' group. In this embodiment, R and R' may be the same or different, and may be hydrogen, alkyl or aryl. A preferred —NRR' group is —NH$_2$.

By the term "alkyl amine group" herein is meant an alkyl group, as defined above, with a —NRR' group, as defined above. As defined above, the alkyl group may be substituted or unsubstituted. Preferred alkyl amine groups are n-propylamine and n-butylamine.

By the term "alkyl alcohol" herein is meant an alkyl group with an —OH group. As defined above, the alkyl group may be substituted or unsubstituted. The alkyl alcohol may be primary, secondary or tertiary, depending on the alkyl group. In a preferred embodiment, the alkyl alcohol is a straight chain primary alkyl alcohol, generally containing at least 3 carbon atoms. Preferred alkyl alcohols include, but are not limited to, n-propyl alcohol, n-butyl alcohol. n-pentyl alcohol, n-heptyl alcohol, or n-octyl alcohol.

By the term "alcohol" herein is meant an —OH group.

In a preferred embodiment, one of $R_1$–$R_8$ is either a polypeptide or a nucleic acid. When one of the R groups is a polypeptide or nucleic acid, it is preferred that only one of the R groups is a polypeptide or nucleic acid. That is, a single R group of the cobalt compound is either a polypeptide or a nucleic acid. In an alternative embodiment, more than one of the R groups may be a polypeptide or a nucleic acid. When the Co of Formula 1 is Co(III), at least one of $R_1$, $R_2$, $R_3$, $R_4$, $R_5$, $R_6$, $R_7$ and $R_8$ is either a polypeptide or a nucleic acid.

By the term "polypeptide" herein is meant a compound ranging from about 2 to about 15 amino acid residues covalently linked by peptide bonds. Preferred embodiments utilize polypeptides from about 2 to about 8 amino acids, with about 4 to about 6 being the most preferred. Preferably, the amino acids are naturally occurring amino acids in the L-configuration, although amino acid analogs are also useful, as outlined below. Under certain circumstances, the polypeptide may be only a single amino acid residue. Additionally, in some embodiments, the polypeptide may be larger, and may even be a protein, although this is not preferred. In one embodiment, the polypeptide is glycosylated.

Also included within the definition of polypeptide are peptidomimetic structures or amino acid analogs. Thus for example, non-naturally occurring side chains or linkages may be used, for example to prevent or retard in vivo degradations. Alternatively, the amino acid side chains may be in the (R) or D-configuration. Additionally, the amino acids, normally linked via a peptide bond or linkage, i.e. a peptidic carbamoyl group, i.e. —CONH—, may be linked via peptidomimetic bonds. These peptidomimetic bonds include CH$_2$—NH—, CO—CH$_2$, azapeptide and retroinversion bonds.

As used herein, "nucleic acid" may refer to either DNA or RNA, or molecules which contain both deoxy- and ribonucleotides. Generally, the nucleic acid is an oligonucleotide, ranging from about 3 nucleotides to about 50 nucleotides, with from about 12 to about 36 being particularly preferred, and at least 21 nucleotides being especially preferred. When the nucleic acid is used solely to confer solubility, the nucleic acid may be smaller, and in some embodiments may be a single nucleotide. The nucleotides may be naturally occurring nucleotides, or synthetic nucleotides, and may be any combination of natural and synthetic nucleotides, although uracil, adenine, thymine, cytosine, guanine, and inosine are preferred. As is more fully described below, the nucleic acids include genomic DNA, CDNA and oligonucleotides including sense and anti-sense nucleic acids. The nucleic acid may be double stranded, single stranded, or contain portions of both double stranded or single stranded sequence. In a preferred embodiment, for example when the nucleic acid is used to target a zinc finger transcription factor, the nucleic acid is double stranded, as zinc fingers bind to the major groove of double stranded nucleic acids.

A nucleic acid will generally contain phosphodiester bonds, although in some cases, as outlined below, a nucleic acid may have an analogous backbone, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 96:141 91986)), phosphorothionate, phosphorodithioate, O-methylphosphoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); Nielsen, Nature, 365:566 (1993)). These modifications of the ribose phosphate backbone may be done to facilitate the addition of cobalt compounds, as outlined below, or to increase the stability and half-life of such molecules in physiological environments.

In one embodiment, the polypeptide or nucleic acid is chosen just to confer solubility on the Co(II) or cobalt compound, and thus the actual sequence of amino acid residues or nucleotides is not critical. Alternatively, as outlined below, the amino acid residues or nucleotides are chosen to target a particular protein or enzyme.

In a preferred embodiment, one of $R_1-R_8$ is either a polypeptide or a nucleic acid that is used to target the cobalt compound to a particular target protein. That is, the cobalt compound is covalently linked to a polypeptide or nucleic acid that will specifically bind or associate with a target protein. In a preferred embodiment, the cobalt compound containing a polypeptide as one of the R groups inhibits a protein, which may or may not be an enzyme. By "inhibition of a protein" herein is meant that a biological activity of the protein is decreased or eliminated upon binding of the inhibitor. In the case of enzymes, inhibition results in a decrease or loss of enzymatic activity. For example, polypeptides comprising protease substrates or inhibitors are used as an R group on the cobalt compounds, to form cobalt compounds that will selectively inhibit the protease. Similarly, a cobalt compound containing an R group comprising a nucleic acid that specifically binds to a particular transcription factor is used to selectively inhibit the transcription factor. These targeted cobalt compounds preferentially bind to the target site on the protein, favoring that site over non-specific binding to other sites or other proteins. This makes the resulting compound more effective at lower concentrations since fewer molecules are wasted at other sites and minimizes the side-effects due to inhibition of other proteins. Secondary interactions also increase the time spent at the target, giving more opportunity for ligand exchange.

In designing a cobalt compound for a particular protein, it is to be understood that the high affinity of the cobalt compound for an imidazole moiety, or the other possible reactive axial ligand moieties, is such that the cobalt compound need not be a perfect fit in the active site. Rather, what is important is that the cobalt compound be able to approach the target axial ligand moiety. For targeting active site residues of enzymes, for example, the cobalt compounds should generally not be larger than typical enzyme substrates or inhibitors. The gross structure and surface properties of the cobalt compound reagent will determine its outer sphere interaction with the desired biological active site. Specificity in outer sphere interactions is optimized by variations in size, charge flexibility, stereochemistry, and surface properties of the cobalt compound reagent. Thus, in designing an appropriate inhibitor, the characteristics of the protein or enzyme target are exploited. In addition, as is shown in the examples, increasing the local concentration of the cobalt compound at or near the active site of the protein is sufficient to increase the binding of the cobalt compound and thus the inhibition of the biological activity of the protein, effectively decreasing the $K_m$ or $K_i$ values, in the case of enzymatic inhibition.

In a preferred embodiment, at least one of $R_1-R_8$ of Formula 1 is a polypeptide. In this embodiment, the polypeptide is chosen on the basis of the target protein or enzyme to be inhibited.

For example, when the target enzyme is a protease, the polypeptide will mimic or comprise an enzyme substrate or the reactive site of an inhibitor. When the polypeptide comprises an inhibitor, the inhibitor may be either a reversible or irreversible inhibitor. The sequence of the polypeptide is chosen to allow the binding of the polypeptide to the active site of the protease.

The polypeptide and the site of attachment of the polypeptide to the cobalt compound, will be chosen to maximize the interaction of the cobalt with the active site histidine. That is, as is explained below, the polypeptide may be attached to the cobalt compound at the N-terminal end, the C-terminal end, or internally, via one or more amino acid side chains.

As is well known in the art, the active site histidine of many enzymes is close to the S1–S1' position of the enzyme's substrate (or inhibitor) binding site. Examples include the serine and cysteine proteases. Thus, in a preferred embodiment, the polypeptide is chosen to allow optimum interaction of the cobalt compound with the active site histidine. For example, the polypeptide may comprise roughly the P4 through P1 residues of a substrate or inhibitor (which occupy the S4 to S1 positions of the enzyme's binding site), and be attached at the C-terminal end (P1) to the cobalt compound, to maximize the steric interaction of the cobalt compound with the active site of the enzyme, and particularly the active site histidine. Alternatively, the polypeptide may comprise the P1' through P4' residues (corresponding to the S1' to S4' positions). with attachment at the N-terminus (P1'). In a further embodiment, the polypeptide spans the P1–P1' site, but has an internal attachment at or near the P1 or P1' residues, to similarly maximize the interaction of the cobalt compound with the active site histidine. These types of attachments are described below. However, as noted above, the interaction need not be perfect to allow inhibition, since it appears that increasing the local concentration of the cobalt compound near the active site is sufficient.

Thus, the present invention allows a known enzymatic substrate to be used as an inhibitor, as well as increasing the efficiency of known inhibitors, for example via decreasing the $K_i$. A wide variety of enzyme substrates and inhibitors for a variety of proteases containing either an active site histidine or an essential metal ion coordinated by a histidine are known in the art. In addition, the morphological properties of enzymes for which the crystal structures are known are used to design appropriate cobalt compounds. Alternative embodiments utilize known characteristics about surface charge and hydrophobicity, and substrate and inhibitor specificity.

In a preferred embodiment, the $K_1$ of the polypeptide inhibitor is decreased as a result of attachment to the cobalt compound. That is, the inhibitor becomes a better inhibitor as a result of the attachment of the cobalt compound. Thus, the cobalt compound is effective at lower concentrations since fewer molecules are wasted at other sites.

In a preferred embodiment, at least one of the R groups is a nucleic acid used to target the cobalt compound to a particular protein or enzyme. For example, the target protein can be a nucleic acid binding protein that has at least one histidine that is important in biological activity, such as a zinc finger protein.

As is known for zinc finger proteins that bind nucleic acids, it appears that each zinc finger interacts or binds to three base pairs of nucleic acid (see Berg. supra). Thus, the actual sequence of the nucleic acid used to target a nucleic acid binding protein will vary depending on the target protein. Nucleic acid sequences and their target binding proteins are known in the art.

As with the polypeptides, the cobalt compound can be attached to the nucleic acid in a variety of ways in a variety of positions; the actual methods are described below. The attachment site is chosen to maximize the interaction of a cobalt-reactive amino acid such as histidine that is essential for metal ion binding (or an active site histidine) with the cobalt compound. In a preferred embodiment, the backbone of the nucleic acid is modified to contain a functional group that can be used for attachment to the cobalt compound. This functional group may be added to either the 5' or 3' end of the nucleic acid, or to an internal nucleotide. For example, the nucleic acid may be synthesized to contain amino-modified nucleotides using techniques well known in the art (see for example Imazawa et al., J. Org. Chem. 44:2039–2041 (1979); Miller et al., Nucleosides, Nucleotides 12:785–792 (1993); and WO95/15971, and references cited therein). In this embodiment, amine groups are added to the ribophosphate backbone at the 2' or 3' position, thus allowing the attachment of the nucleic acid to the cobalt at either the 5' or 3' end, or to an internal nucleotide. These amine groups are then used to couple the nucleic acid to the cobalt compound. Alternatively, nucleotide dimers, containing phosphoramide, phosphorothioate, phosphorodithioate, or O-methylphosphoroamidite linkages may be made, and added to the nucleic acid at any position during synthesis, and the nitrogen or sulfur atom used for attachment using well known techniques, as outlined below. Additionally, the phosphorus atom of the backbone may be used, or linkers, as is known in the art (see for example Thuong et al., Angew. Chem. Int. Ed. Intl. 32:666–690 (1993); and Mergny et al., Nucleic Acid Res. 22:920–928 (1994)).

When Co is Co(II) in Formula 1, at least one of $R_1$, $R_2$, $R_3$, $R_4$, $R_5$, $R_6$, $R_7$ and $R_8$ is hydrophilic such that the Co(II) compound is soluble in aqueous solution. In one embodiment, only one of the R groups is hydrophilic and the other R groups are chosen such that the single hydrophilic R group is sufficient to confer water solubility to the Co(II) compound. In a preferred embodiment, R, is hydrophilic, for example, n-propyl alcohol. In alternative embodiments, two, three, four, five, six, seven or eight R groups are hydrophilic. In a preferred embodiment, the hydrophilic group is either a polypeptide or a nucleic acid.

By "soluble in aqueous solution" herein is meant that the Co(II) compound has appreciable solubility in aqueous solution and other physiological buffers and solutions. Solubility may be measured in a variety of ways. In one embodiment, solubility is measured using the United States Pharmacopeia solubility classifications, with the Co(II) compound being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute). Alternatively, since cobalt containing compounds are generally colored, the appearance of a color upon addition to a colorless aqueous solution indicates an acceptable level of solubility. For example, many Co(II) Schiff's base complexes have a yellow or orange color.

Testing whether a particular Co(II) compound is soluble in aqueous solution is routine, as will be appreciated by those in the art. For example, as noted above, the appearance of a Schiff's base Co(II) complex color upon addition to a colorless aqueous solution indicates solubility. Alternatively, the parts of solvent required to solubilize a single part of Co(II) compound may be measured, or solubility in gm/ml may be determined.

In a preferred embodiment the cobalt compounds depicted in Formula I have a regiospecific hydrophilicity. That is, $R_1$, $R_2$, $R_3$, and $R_4$, are either hydrogen, alkyl or aryl, and are therefore hydrophobic, and at least one of $R_5$, $R_6$, $R_7$ and $R_8$ is hydrophilic. However, other combinations resulting in amphiphathic characteristics are also possible, as will be appreciated by those in the art. This is particularly desirable since this regiospecific hydrophilicity allows better positioning of the cobalt compound in or near the active site or on the surface of a protein or enzyme, as is discussed below. Without being bound by theory, it appears that this regiospecific hydrophilicity/hydrophobicity allows the cobalt compound to more efficiently interact with the protein or enzyme, which generally displays both hydrophobic and hydrophilic regions.

Particularly preferred embodiments of the present invention include the structure depicted in Formula 3, wherein $R_1$ is n-propyl alcohol, $R_2$ is hydrogen, $R_3$ is methyl, $R_6$ is methyl, $R_7$ is hydrogen, $R_8$ is methyl, and $R_4$ and $R_5$ are hydrogen:

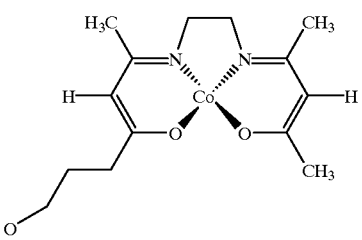

Formula 3

In this embodiment, the Co can be either Co(II) or Co(III).

The structures depicted in Formulas 4 and 5 are also preferred:

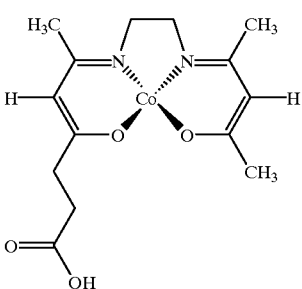

Formula 4

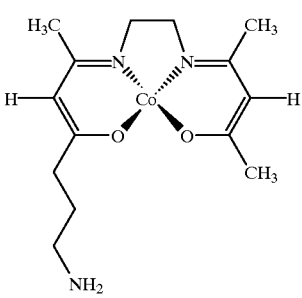

Formula 5

In a preferred embodiment, the cobalt complexes may have groups that alter the redox potential, oxidation stability, or ability of the compound to exchange an axial ligand. For example, many of the Co(II) complexes of the invention are sensitive to air oxidation. That is, in the presence of atmospheric oxygen, they may be oxidized. Thus in a preferred embodiment, the Co(II) complexes are synthesized and utilized in the absence of air.

Thus, in a further embodiment, the Co complexes are additionally modified to make them air stable compounds. For example, replacement of a methyl R group in a complex of the invention with a trifluoromethyl group results in a positive shift of the metal oxidation potential, stabilizing, the metal complex with respect to air oxidation. For example, 1.1.1-trifluoro-2,4-pentalnedionie is commercially available, and may be used to synthesize trifluoromethyl derivatives of the Co(II) complexes disclosed herein. Further well known modifications such as chlorination of the Schiff's base macrocycle also greatly enhance the stability of these complexes with respect to air oxidation. Thus, the use of trifluoromethyl groups alone or in conjunction with chlorination of the macrocycle will result in a soluble air stable Co(II) macrocycle complex.

These types of derivatives may also be made to adjust the redox potential of complexes to modulate their reactivity with other compounds.

Similarly, the addition of electron donating or electron withdrawing (groups may affect the activity of the cobalt compound with respect to the ability to exchange an axial ligand. As shown in the examples, the addition of trifluoromethyl R groups at the $R_1$ and $R_8$ positions basically eliminates the reactivity of the Co(III) compound towards new axial ligands. Electron withdrawing or donating groups are preferably added at the $R_1$ and/or $R_8$ positions, as this is easiest for synthesis, as well as the preferred position for electronic coupling. The $R_2$ and/or $R_7$ positions are also preferred. It is also possible to put electron donating groups at the $R_3$ and $R_6$ positions, but if $R_3$ and/or $R_6$ contain an electron withdrawing group then the compound may be difficult to synthesize using the schemes depicted herein. Suitable electron withdrawing groups include, but are not limited to, halides (F, Cl, Br, I, in decreasing order of electron withdrawing strength), phenyl and substituted phenyl groups such as nitro-phenyl, amines and quaternary amines, thiols, nitro groups, carboxy groups, nitrile, alkynes and alkanes, sulfonyls, and others known in the art. Suitable electron donating groups include, but are not limited to, —$OCH_3$, methyl, carboxylate, and ether.

Once the R groups are chosen, the preparation of the cobalt compounds of the invention proceeds as outlined below.

Generally, the cobalt compounds of the invention are synthesized as generically disclosed below in Scheme 1, using the general methods of Costa et al., *J. Organometal. Chem.*, 6:181 (1966), which describes the preparation of derivatives of the components used to make the ligands used in the invention, such as acetylacetone etlhylenediamine (acacen).

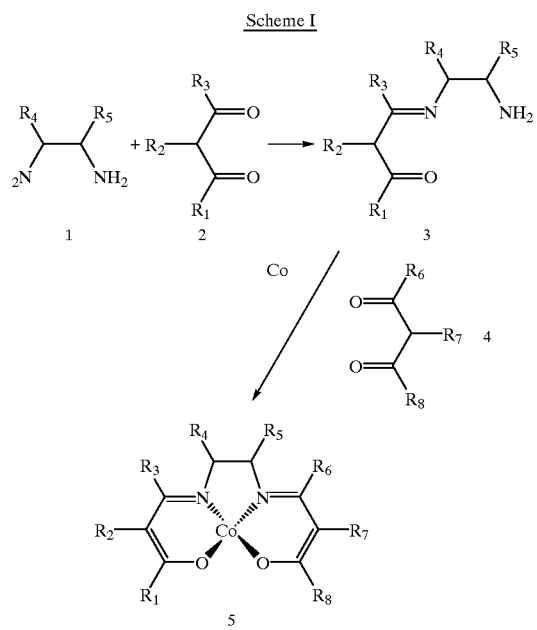

Scheme I

Compounds 1 (etlhylenediamine, "en"), 2 and 4 are generally made using techniques well known in the art. Compounds 2 and 4 are aliphatic β-diketones, and compound 2 is an aliphatic amine. It will be understood by those skilled in the art that compounds 2, 3 and 4 are the resonance structures of compounds 6, 7, and 8 shown below in Scheme 11. Compounds 6 and 8 are acetylacetone derivatives ("acac"), and compound 7 is the "monoacacen" product.

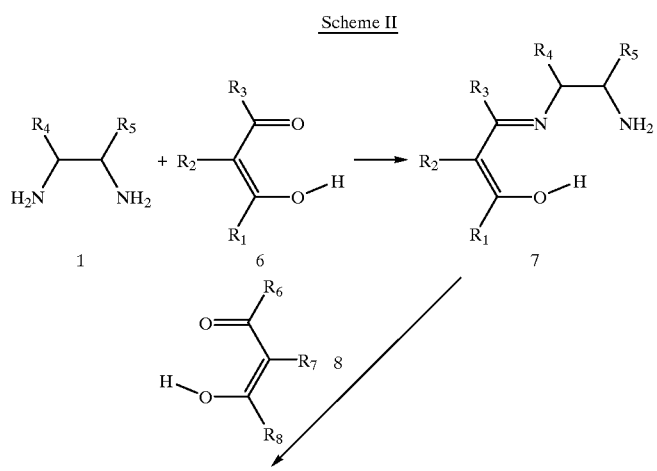

Scheme II

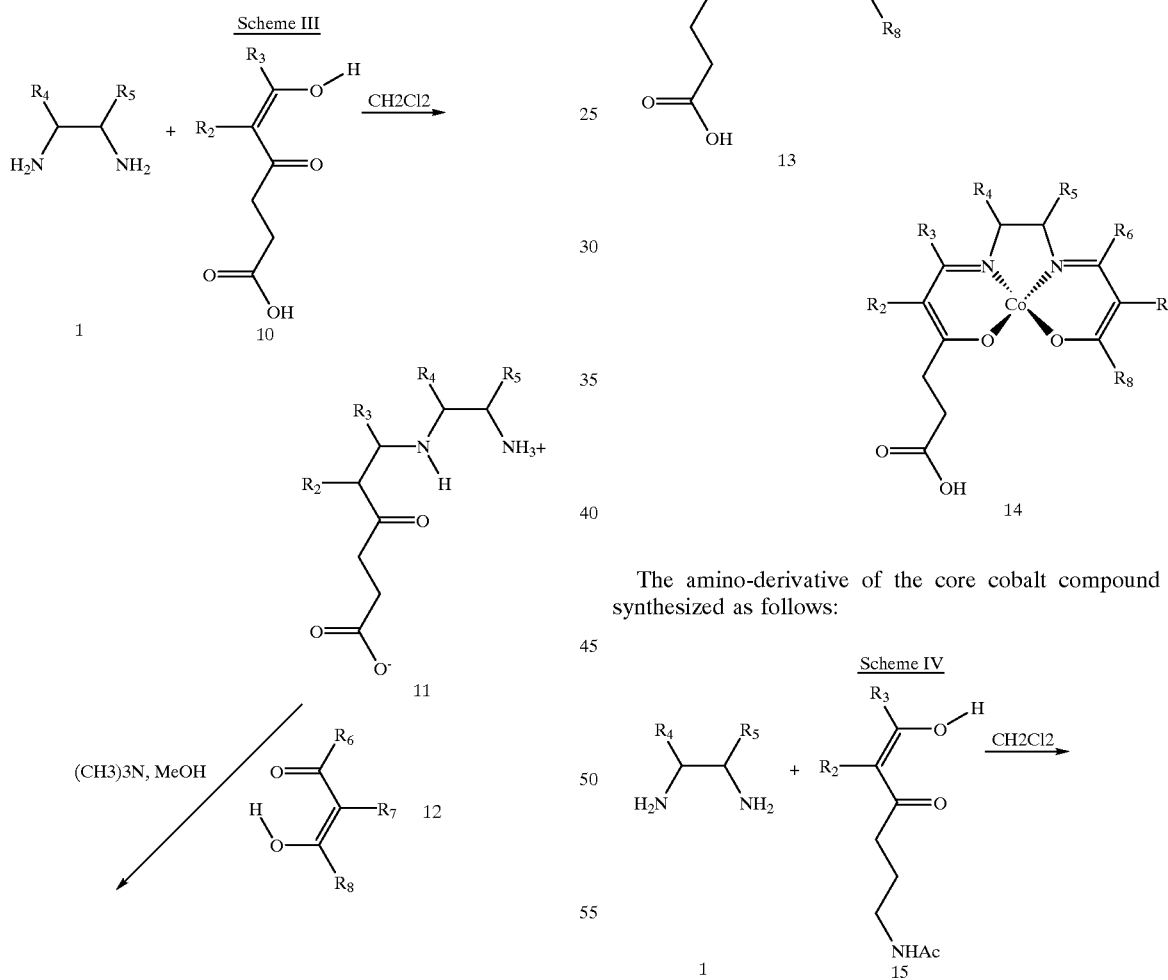

When the Co is Co(III), the axial ligands are usually added in the last step. Of particular use for attachment of polypeptide and nucleic acid R groups are cobalt compounds with carboxy and amino groups. Cobalt compounds utilizing carboxylic acids are synthesized as depicted below in Scheme III:

The amino-derivative of the core cobalt compound is synthesized as follows:

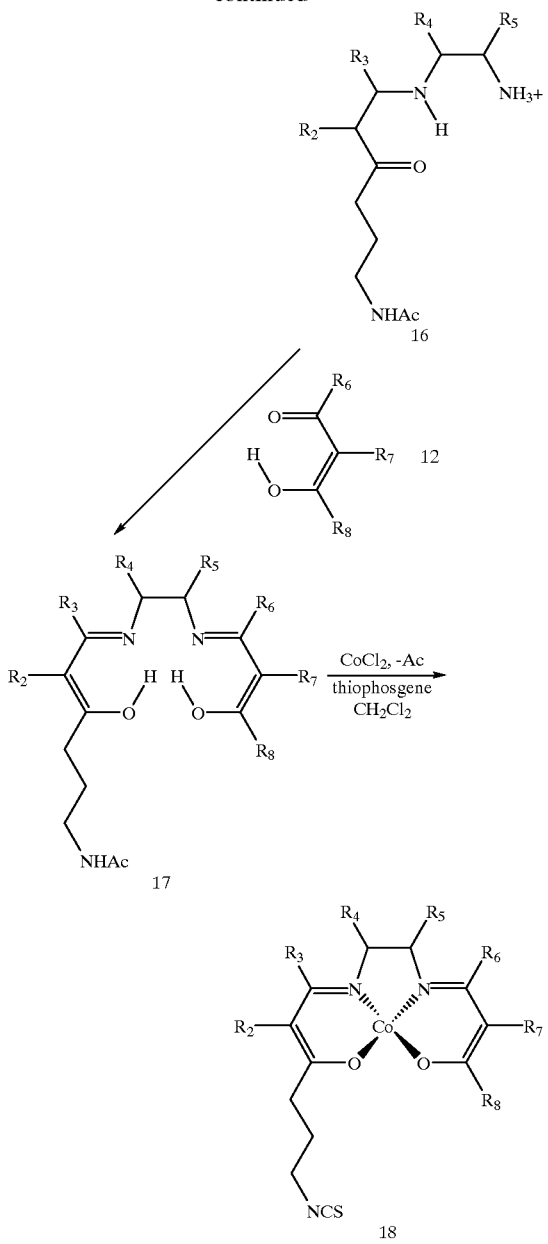

The NCS group may then be used for coupling, as is known in the art.

In the case where the R group is a polypeptide or nucleic acid, the cobalt compounds are generally constructed in three phases. First, the core cobalt compound is synthesized with a functional moiety that can be used to couple the polypeptide or nucleic acid. For example, the core cobalt compound is made with an amine, a carboxy or a sulfhydryl group. Next, the R group, comprising a polypeptide or nucleic acid, is made, which also contains a functional moiety that can be used for attachment. In some instances, other reactive groups of the polypeptide or nucleic acid are protected to prevent them from reacting with the functional group of the core cobalt compound. For example, amino acid side chains containing amino groups, such as arginine, may need to be protected to prevent the side chain from reacting, although in some embodiments the attachment is done via a functional moiety of an amino acid side chain.

Protecting groups and techniques are well known in the art. Once the core cobalt compound and the R group are made, they can be attached by reacting the functional groups. In some instances, the linkage is direct; for example a cobalt compound containing a carboxy R group may be directly linked to an amino terminus of a polypeptide, as is depicted in the Examples. C-terminal attachment may be done using a cobalt compound with a amino functional moiety. As is known in the art, this direct linkage may be done in organic solvents or alternatively using coupling reagents such as 1-(3-dimethylaminopropyl )-3 -ethylcarboiimide (EDC) (see generally, March, *Advanced Organic Chemistry*, 3rd Ed. Kiley & Sons. Inc. (1985); see also the 1994 Pierce Chemical Company catalog, technical section on cross-linkers, pages 155–200, incorporated herein by reference).

In a preferred embodiment, the linkage between the two functional moieties may utilize a linker, also well known in the art. For example, two amino groups may be linked via a stable bifunctional groups as are well known in the art, including homobifunctional and heterobifunctional linkers (see Pierce Catalog and Handbook, pages 155–200). In an additional embodiment, carboxy groups (either from the polymer or from the cell targeting moiety) may be derivatized using well known linkers (see the Pierce catalog). For example, carbodiimides activate carboxy groups for attack by good nucleophiles such as amines (see Torchilin et al.. Critical Rev. Therapeutic Drug Carrier Systems, 7(4):275–308 (1991), expressly incorporated herein). Sulfhydryl groups may be added to amines or carboxy groups with heterobifunctional linkers (see the Pierce catalog).

It should be understood that the attachment may be done in a variety of ways, including those listed above. What is important is that manner of attachment does not significantly alter the functionality of the polypeptide or nucleic acid; that is, they are still able to bind to the target protein. As will be appreciated by those in the art, this is easily verified.

As will be appreciated in the art, a number of functional groups of the polypeptide and nucleic acid may be used for covalent coupling. Alternatively, the polypeptide may be derivatized to contain a functional moiety, such as through the addition of a linker containing a functional moiety. When a polypeptide is to be used as an R group, a preferred embodiment utilizes an amino group of the polypeptide. The N-terminal amino group may be used, or alternatively, an amino group of an amino acid side chain, such as the amine groups of arginine, asparagine, glutamine, lysine, histidine and tryptophan. Similarly, the linkage may be accomplished using the sulfur atoms of the side chains of methionine or cysteine. The carboxy groups of the side chains of glutamic acid and aspartic acid may also be used.

When the R group is a nucleic acid, a variety of positions may be used as the site of covalent attachment to the cobalt compound. In a preferred embodiment, the ribophosphate backbone of the nucleic acid is modified to contain a functional moiety (see for example Meade et al.. Angewandte Chemie, English Edition, 34(3):352–354 (1995), and references cited therein; Imazawa et al.. supra, Miller et al., supra.). For example, in a preferred embodiment, an amino group is added at the 2' or 3' position of the sugar using techniques well known in the art. In one embodiment, this is done by adding additional nucleotides that have an added amino group to the nucleic acid; that is, as shown in the Examples, one or more "extra" nucleotides is added to the targeting nucleic acid. Alternatively, the phosphodiester linkage between two nucleotides may be altered to form phosphoramide, phosphorothioate, phosphorodithioate, or O-methylphosphoroamidite linkages, as is known in the art. The nitrogen or sulfur atoms are then used as functional moieties. The nucleotide dimer, containing the altered linkage, may be added to the nucleotide at any position. Functional groups on the nucleotide bases themselves may also be used, such as the amino groups on adenosine and cytosine, or modified bases such as is known for thymine (see for example Telser et al., J. Amer. Chem. Soc. 111:7221–7226 (1991); Unglisch et al., Angew. Chem 103:629–646 (1991); Angew. Chem. Int. Ed. Engl. 30:613–629 (1991); Goodchild, Biocnjugate Chem. 1:165–187 (1990); and Brun et al., J. Amer. Chem. Soc. 113:8153–8159 (1991)). Then the nucleic acid containing the functional group may be added to the cobalt compound either directly or via a linker, as is outlined above for polypeptides.

Once synthesized, the cobalt compounds of the invention find use in a number of applications. At the broadest level, the Co(II) compounds are useful as reducing agents in aqueous solution.

In one embodiment, the cobalt compounds of the invention are useful as general bacteriostatic or bactericidal agents, antimicrobial agents and/or antiviral agents, for both topical and other therapeutic applications. For example, topical antimicrobial agents may be useful in cleaning and disinfectant compositions, as will be appreciated in the art. Therapeutic uses of antimicrobial and antiviral agents are also well known.

The compounds are assayed for antiviral, antimicrobial and antibacterial activity using techniques well known in the art; for example, bactericidal activity may be measured using the techniques outlined in example VI of U.S. Pat. No. 5,049,557. Both in vitro and in vivo antiviral activity may be measured using the techniques outlined in U.S. Pat. No. 5,210,096.

The cobalt compounds of the invention can also be used to label proteins. The Co(II) compounds of the invention are preferably made with no axial ligands, and the Co(III) compounds are generally made with two axial ligands. Upon incubation with a protein, certain moieties on the protein will become axial ligands, resulting in a tightly bound protein-cobalt compound complex. Since cobalt-containing compounds may be detected spectrophotometrically, the result is a labeled protein. The preferred axial ligand from a protein is the imidazole side chain of histidine. Thus, a protein with one or more histidine residues either at the surface of the protein or otherwise accessible to the solvent can be labeled using the cobalt compounds of the invention.

In this embodiment, the cobalt compounds of the invention are added or contacted with the target protein. The excess cobalt compound may be separated, and the labeled protein, with the attached Co(III) compound, is detected spectrophotometrically. The Co(III) compounds are generally detected at 280, 338. and 451 nm, although a broad range from 280 to 500 nm may be useful.

The stoichiometry of the bound cobalt compound to protein will vary depending on the number of potential axial ligands in or at the active site or on the surface of the protein, and may be determined spectrophotometrically, as is understood in the art. Thus, for example, a protein which has foul accessible histidines will generally bind four cobalt compounds, etc.

Thus, the cobalt compounds of the present invention are also useful in probing the surface characteristics of a protein.

When used to bind or label proteins, the cobalt compounds can be coupled, using standard technology, to affinity chromatography columns. These columns may then be used to separate proteins from a sample. For example, depending on the specificity of the cobalt complex, proteins may be removed from a sample, or specific proteins, such as those containing histidines at or near the active site may be separated from other components of the sample. In a preferred embodiment, the cobalt compounds are useful as enzyme inhibitors. The mechanism of inactivation is similar to the mechanism of protein labeling. In this embodiment, an enzyme has one or more moieties capable of binding in an axial position in the cobalt compounds of the invention. One or more of such moieties are also functionally important for enzymatic activity, and arc inactivated upon contact with the cobalt compounds of the invention.

For example, enzymes which have histidine as an active site catalytic residue or have histidines which are functionally important for enzymatic activity are particularly preferred. Enzymes such as the serine proteases (trypsin, subtilisin, chymotrypsin, elastase, thrombin, factor Xa, lysozyme, and others known in the art), cysteine proteases such as the cathepsins and interleukin converting enzyme; RNAse H, thermolysin and lactate dehydrogenase all have active site histidines and thus may be inhibited with the compounds of the present invention.

In this embodiment, a cobalt compound is contacted with the target enzyme. The imidazole side chain of an active site histidine binds to the cobalt compound as an axial ligand. In the case of Co(II), this occurs with a simultaneous or rapid oxidation of the Co(TI) compound to form an enzyme-Co (III) compound complex. This is termed "redox coupling".

The binding (and oxidation, in the case of the Co(II) compound) results in the inhibition of the enzyme. The exact mechanism of the inactivation is unknown; however, several possibilities exist. The bound cobalt compound, which after binding and oxidation is a Co(III) compound, may sterically interfere with catalytic activity, i.e. it may be bound in or near the catalytic active site. Alternatively, the bound cobalt compound may interfere with the catalytic mechanism. i.e. by binding to a catalytic histidine. Additionally in the case of Co(II), it is also possible that a functionally important moiety at the active site is reduced by the Co(II) compound, and thus the enzyme is inactivated.

In a preferred embodiment, the inactivation of, the enzyme by the cobalt compound inhibitor is effectively irreversible.

In alternative embodiments, the reactive axial ligand from the enzyme is the indole side chain of tryptophan or the side chains of cysteine, methionine. arginine, lysine, asparagine, glutamine, aspartate or glutamate. As outlined above, the availability of these moieties may depend on the pH of the solution containing the protein or enzyme, since in the protonated state these moieties are not good electron donors suitable as axial ligands. Thus, enzymes with these groups within the active site, or enzymes which have functionally important tryptophans, cysteines, or methionines may be inactivated by the cobalt compounds of the present invention, as outlined above.

In an additional embodiment, metalloproteins are inactivated with the cobalt compounds of the present invention. Generally, the metals of metalloproteins have ligands such as histidine, cysteine and methionine. If one or more of these residues are inactivated using these cobalt compounds, the binding of the metal atom may be decreased or eliminated, thus reducing or eliminating biological activity. Particular metalloproteins include, but are not limited to, nucleic acid binding proteins such as "zinc finger" proteins and hemerythrin. Zinc finger proteins utilize histidine and cysteine to bind zinc ions (see Berg, Ann. Rev. Biophys. Biophys. Chem 19:405–421 (1990), Berg, Science 232:485 (1986), and Berg, Prog. Inorg. Chem. 37:143 (1989), hereby expressly incorporated by reference). Zinc finger proteins have been shown to bind nucleic acids and thus play a role in a variety of gene regulatory processes. Zinc finger proteins include transcription factors and other nucleic acid-binding, and gene-regulatory proteins (see Berg, Science, supra), and are found in eukaryotes, prokaryotes, and viruses. Other zinc finger proteins suitable for inactivation by the compounds of the present invention include the nucleic acid binding domain of steroid and thyroid hormone receptors and the human oncogene product GLI (see Pavletch et al., Science 261:1701 (1993), Kinzler et al., Nature 332:371 (1988)), that contains five zinc finger domains. In a preferred embodiment, one or more of the zinc finger domains utilizes at least one histidine to bind zinc, with the proteins that utilize two histidines being, preferred. In some cases the metal is bound exclusively by cysteines.

When the metalloprotein is a metalloenzyme, displacement of the active site metal by the cobalt complex may modulate enzyme activity. Such metalloenzymes include, but are not limited to, the carboxypeptidases, carbonic anhydrase, thermolysin, collagenase, histidinol dehydrogenase, leukotriene A4 hydrolase, adenosine deaminase, superoxide dismutase, alcohol dehydrogenase, lactate dehydrogenase, stromalycin, aminoacyclase, tryptophanyl-tRNA synthetase, and others known in the art.

In a preferred embodiment, serine and cysteine proteases are inhibited.

In a preferred embodiments the enzyme to be inhibited is carbonic anhydrase. Carbonic anhydrase has been implicated in diabetes, ocular disease such as glaucoma, and seizures and convulsions. Accordingly, inhibitors of carbonic anhydrase, such as the Co(II) complexes of the present invention, are useful in the treatment of these conditions.

Thus, in one embodiment, the Co(II) complexes are useful in the treatment of elevated intraocular pressure and glaucoma. Carbonic anhydrase has been implicated in elevated intraocular pressure, and carbonic anhydrase inhibitors have been shown to be efficacious in decreasing this pressure in animals and humans (see Sharir et al., *Experimental Eye Res.* 58(1):107–116 (1994); Rassam et al., *Eye* 7(Pt 5):697–702 (1993), Gunninig et al., *Graefes Archive for Clinical and Experimental Ophthalmology* 231(7):384 (1993)).

In an additional embodiment, the Co(II) compounds are useful in the treatment of seizures and convulsions. Carbonic anhydrase II deficient mice have been shown to have increased resistance to chemically induced seizures, and pretreatment with carbonic anhydrase inhibitors has been shown to increase the resistance of normal mice to chemically induced seizures. See Velisek et al., *Epilepsy Res.* 14(2):115–121 (1993).

In a further embodiment, the Co(II) compounds are useful in the treatment of diabetes and abnormal renal function. Elevated levels of carbonic anhydrase have been associated with metabolic diseases like diabetes mellitus and hypertension, and carbonic anhydrase inhibitors have been suggested for treatment. See Parui et al., *Biochem. International* 26(5):809–820 (1992); Parui et al, *Biochem. International* 23(4):779–89 (1991); Dodgson et al., Arch. *Biochem. Biophys.* 277(2):410–4 (1990); Hannedouche et al., *Clinical Sci.* 81(4):457–64 (1991).

In a preferred embodiment, the cobalt compounds find use in the inhibition of proteins and enzymes of tumor cells. As outlined above, Co(III) "acacen" compounds can exchange an axial ligand for a different one by a dissociative mechanism with the slow loss of one axial ligand to form a five coordinate intermediate, followed by binding to another suitable ligand. For most cobalt complexes, ligand exchange is a slow process because there is a large loss of ligand field stabilization energy when a ligand is removed from an octahedral $d^6$ complex (see Huheey et al., *Inorganic Chemistry: Principles of Structure and Reactivity,* 4th Ed. HarperCollins. N.Y., chapter 13). Generally, the exchange is slow; for example, $[Co(III)(acacen)(NH_3)_2]Cl$ in water with excess imidazole exchanges ammonia for imidazole with a half-life under an hour at 25° C., with the rate of exchange increasing with temperature. However, reduction to cobalt (II) puts an electron into the antibonding $d_{z2}$ orbital, labilizing the axial ligands. Typical one-electronic reduction potentials with irreversible loss of an axial ligand are around –360 mV vs NHE, (Darbieu et al., Transition Met. Chem., 7:149 (1982)). This property may be exploited as a "redox switch" to control the activity of the cobalt compound. For example, certain regions within tumors are often oxygen-starved due to high metabolic demands and inadequate blood supply; therefore, reductive reactions might be more favorable in such an environment than in a healthy cell (see A. C. Sartorelli, *Cancer Research,* (1988), 48, 775; Brown et al., J. Nat. Cancer Inst. 83:178 (1991)).

Raising the reduction potential of a cobalt acacen compound with substituents such as halides may place it high enough for reduction to occur readily in tumor cells, but not in healthy cells. Ware and coworkers use a similar approach to attempt selective release of cobalt-bound cytotoxins in cancer cells (see Ware et al., supra).

Testing the efficacy of the cobalt compounds as inhibitors is routine, as will be appreciated in the art. When the target protein is an enzyme, testing is similar to testing any enzyme inhibitor, as is known in the art. Generally, the enzyme is assayed in the presence and absence of the putative inhibitor, and kinetic parameters are calculated as is known in the art.

The amount of cobalt compound inhibitor needed to inhibit a given enzyme will vary depending on the number of other reactive axial ligands on the Surface of the enzyme, as is outlined above for protein labeling. For example, an enzyme with an active site histidine and two other "surface" histidines will generally require at least a 3:1 ratio of cobalt compound inhibitor:enzyme. The total amount bound to the enzyme may be determined spectrophotometrically, as outlined above.

In a preferred embodiment, the Co(II) compound inhibitors are generated in situ by reducing the corresponding Co(III) compound. By "corresponding Co(III) compound" herein is meant a Co(III) compound which has the identical R groups as the Co(II) compound. Generally, the Co(III) compounds are synthesized with axial ligands, such as, but not limited to, amines, 2-methyl imidazole, and water.

In this embodiment, the Co(III) compound is synthesized, and then added to the enzyme under conditions which can result in the reduction of the Co(III) to Co(II). This may be done in several ways. For example, the in situ environment of the enzyme, whether it be in vitro or in vivo, may be a reducing environment for the Co(III) compound, such that the Co(III) is reduced to Co(II). Alternatively, the Co(III) compound may contain an electron acceptor group as one of the R groups, such that in a given in situ environment, the electron acceptor group will pick up an electron and donate the electron to the Co(III), thus reducing it to the Co(II) form. Suitable electron acceptor groups include, but are not limited to, cations such as methyl violgen (N-N-dimethyl 4,4' bipyridine), or ethyl or propyl violgen, as is understood in the art. Additionally, the reduction potential of the compound may be tailored such that introducing the compound into a particular environment causes reduction; for example, by glutathione in physiological systems. The resulting, Co(II) compound then reacts with the reactive axial ligands of the enzyme to inhibit the enzyme as outlined above. Thus, the Co(II) compound is generated in situ; that is, a Co(III) compound is added to an enzyme, is reduced to the Co(II) form, which in turn inhibits the enzyme. In this embodiment, the Co(III) compounds may be inert with respect to a selected enzymatic target in a given oxidation state, yet inactivate the enzyme target in a second oxidation state. This mechanism allows the in situ addition of a cobalt compound, whether in vitro or in vivo, in an inactive form, with activation to the Co(II) compound form in a particular reducing environment.

The compounds of the present invention may be formulated into pharmaceutical compositions, and administered in therapeutically effective dosages. By "therapeutically effective dose" therein is meant a dose that produces the effects for which it is administered. The exact dose will depend on the disorder to be treated and the protein to be inhibited, and will be ascertainable by one skilled in the art using known techniques. In a preferred embodiment, the pharmaceutical compositions of the invention are in a water soluble form, and contain a pharmaceutically acceptable carrier in addition to the cobalt compound. The pharmaceutical compositions may be administered in a variety of ways, including, but not limited to, orally, subcutaneously, intravenously, intraperitoneally, or topically.

Also provided are methods for inhibiting a selected protein or enzyme with the cobalt compounds of the invention. In this embodiment, the target protein is contacted or exposed to a cobalt compound. In a preferred embodiment, the cobalt compound has the structure depicted in Formula 1. The cobalt compound can be targetted to a particular protein by the addition of a polypeptide or a nucleic acid.

Also provided are methods for inhibiting a zinc finger protein, comprising contacting a zinc finger protein with a cobalt compound. By "inhibiting a zinc finger protein" herein is meant that the biological activity of the zinc finger protein is decreased or eliminated upon exposure to the cobalt compound. Generally, when the zinc finger protein is a nucleic acid binding protein, this means that the zinc finger will no longer bind the nucleic acid to a significant degree. Various prior art Co(III) compounds are well known in the art, (see U.S. Pat. Nos. 4,866,054, 4,866,053, 5,049,557, 5,106,841, 5,142,076, and 5,210,096). These compounds, depicted below in Formula 6, as well as the compounds embodied in Formula 1, have utility in the inactivation of zinc finger proteins. Accordingly, in this embodiment, when Co is Co(III), there is no requirement that at least one of $R_1$ to $R_8$ is either a polypeptide or a nucleic acid, although this is preferred. Likewise, when Co is Co(II), there is no requirement that at least one of the R groups is hydrophilic, although this is preferred.

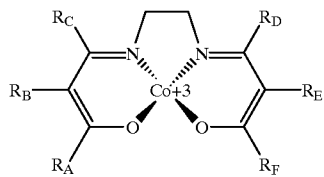

Formula 6

In Formula 6. $R_A$ and $R_F$ are the same or different and each is an alkyl group, a phenyl group or a substituted derivative of a phenyl group. $R_B$ and $R_E$ are the same or different and each is hydrogen, an unbranched alkyl group, a halide or a group having the structure:

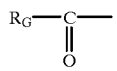

wherein $R_G$ is hydrogen, an alkoxide group, an alkyl group or OH. $R_C$ and $R_D$ are the same or different and each is hydrogen or an alkyl group.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Synthesis of Cobalt Compounds

A sample of [Co$^{III}$(acacen)(NH$_3$),]Cl was obtained as a gilt from Zvi Doni. Acetylacetone, benizoylacetone, etlhylenediamine, and trimethylamine (TEA) were obtained from Aldrich (Milwaukee, Wis.).

Tris(hydroxymethyl)aminomethane (Tris, Trizma Base), polyethylene glycol (PEG 8000) and 1-(3-dimethylaminopropyl)-3-ethylcarboiimide (EDC) were obtained from Sigma (St. Louis, Mo.).

N-(2-hydroxyethyl)piperazine-N'-2-ethanesulfonic acid (HEPES) was from J. T. Baker Phillipsburg, N.J.). Cobaltous acetate tetrahydrate was obtained from FM Science (Gibbstown, N.J.). Human a-thrombin and the assay agent Spectrozyme (H-D-hexahydrotyrosyl-L-alanyl-L-arginine-p-nitroaniline diacetate) were purchased from American Diagnostica (Greenwich, Conn.). Antithrombotic peptides were manufactured as amides by the Beckman Institute Biopolymer Synthesis group at Caltech using solid phase methods. Weak cation exchange resin Sephadex G-25 was from Pharmacia (Uppsala, Sweden). Enzyme reactions were followed spectrophotometrically using a photodiode array spectrophotometer. Ultrafiltration materials were from Amicon (Beverly Mass.). HPLC used Vydac reverse phase columns. $^1$H NMR were obtained on a 300 MHz FT-NMR spectrometer. Solvents used include EM Omnisolve MeOH, Omnisolve CH$_2$Cl$_3$ passed over basic alumina to remove residual acid, Fluka (Bubcs. Switzerland) puriss. MeOH and dioxane, and Quantum Chemical (Tuscola, Ill.) absolute EtOH. Distilled water was prepared by a Barnistead Nanopure system. All other solvents were reagent trade.

Synthesis of hydroxypropyl acacen

To 200 mL of deoxygenated $CH_2Cl_2$ was added 10 mL of acetyl acetone (acac, 0.0974 mol) and cannulated into a 250 ml. addition funnel, which was attached to a 500 mL 3-neck roundbottom flask containing 100 ml. of deoxygenated $CH_2Cl_2$ and 32.6 mL etlhylenediamine (en, 0.488 mol). The solution containing the acac was added dropwise to the en solution. The reaction mixture was extracted with two 50 ml. portions of 0.2 NaPi, pH5.5. The organic layer was separated and placed in a −20° C. freezer overnight. The resulting solution was filtered through fluted filter paper and the solvent was removed in vacuo. The compound was further purified using flash silica gel chromatography using 95:5:0.5 (v:v:v) $CH_2Cl_2$:MeOH:$Et_3$N as the eluanit. The resulting monoacacen was characterized by NMR.

Monoacacen (0.5 g, $3.5 \times 10^{-3}$ mol) was dissolved in 5 mL of ethanol and 7-hydroxy-2,4-heptanedione (0.51 g. $3.5 \times 10^{-3}$ mol) was added. The dione was synthesized as described previously (Detty, M. R. J. Org. Chem., 44:2073–2077 (1979)). The reaction was allowed to proceed for 4 hours and the solvent was removed in vacuo. The sample was purified using flash silica gel chromatography using 93:7 (v:v) $Cl_2Cl_2$:MeOH as the eluant. The resulting hydroxypropyl acacen was characterized by NMR.

Synthesis of Co(II)hydroxypropyl acacen

Hydroxypropyl acacen (0.25 g, $9.4 \times 10^{-4}$ mol) was dissolved in 2 mil of deoxygenated methanol in an inert atmosphere glove box. To this solution was added CO(II) ($CH_3COO—)_2(H_2O)_4$ (0.2338 g, $9.4 \times 10^{-4}$ mol). The mixture was allowed to stir for an additional thirty minutes. The reaction vessel was sealed and the solvent was removed in in vacuo. The compound was used without further purification.

Synthesis of [Co(III)hydroxypropylacacen($NH_3)_2$]$CH_3COO$

Hydroxypropyl acacen was reacted with Co(acetate) as described earlier. However after the reaction vessel was sealed, anhydrous ammonia gas was bubbled through the reaction mixture and subsequently exposed to air. The solvent was removed in vacuo, and the product was purified using an alumina column with neat methanol as the eluant. The sample was characterized by NMR.

Synthesis of Acacen

To 20 mL of ethanol was added 20 mL of acac (0.0973 mol). To this solution was added 6.5 mL of ethylenediamine (0.0973 mol) using an addition funnel. The solution was placed in a refrigerator at 4° C. overnight, and the crystals were triturated three times with anhydrous diethylether (MP=110.1–111.1).

Synthesis of [Co(III)acacen($NH_3)_2$]Cl 249.08 g of cobalt acetate, 6 $H_2O$, (1 mol) was dissolved in 1.750 L methanol and the solution was filtered through Whatman paper No. 1. Acacen (1 mol) was suspended in 150 mL methanol. Nitrogen dried by passage through a silica gel dessicant column was bubbled over the reagents for 15 minutes. The cobalt acetate solution was added dropwise (½ hour) and the orange-brown solution was left to react at room temperature under nitrogen for 2 hours. The flask was opened to air and $NH_3$ gas was bubbled into the solution; the mixture was concentrated on a rotary evaporator. An equivalent of sodium chloride dissolved in a minimum amount of water was added, poured into a wide vessel, and left to crystallize slowly. The brown crystalline powder was filtered, washed with methanol and dried.

Further synthesis of assymetrical or "mixed" ligands "Acacen" (compound 9 in Scheme II): 1 equivalent ethylenediamine in anhydrous EtOH was added to 2 equivalents acetylacetone in EtOH with stirring. After 30 minutes, the mixture was put in the freezer to precipitate a white crystalline solid. The product was collected by vacuum filtration over a coarse glass frit and rinsed with diethyl ether. It can be recrystallized from benzene to desired purity. Purified crystals melted at 111° C.

"Monoacacen" (compound 7 in Scheme II): The 1:1 condensation product of acac and en was prepared according to literature procedures (Cros et al., C. R. Acad. Sc., Ser. II 294:173 (1982)) substituting $CH_2Cl_2$, for chloroform. The resulting yellow oil often contained some acacen (about 10%), which could be removed by flash chromatography on silica using 97 $CH_2Cl_2$/3 MeOH/0.5 TEA either now or after the addition of another diketone.

"Bzacacacen"(the Formula 1 compound with R1, R3 and R6 as methyl, R2 and R7 as hydrogen, and R8 as phenyl): 1 equiv. benzoylacetone in $CH_2Cl_2$ was added to a solution of monoacacen in $CH_2Cl_2$. Removal of solvent gave a white powder containing some acacen impurity. Purification was accomplished by flash chromatography on silica using 97 $CH_2Cl_2$/3 MeOH/ 0.5 TEA.

"Aciden" (compound 11 in Scheme III): A solution of 1 equiv. 4.6-dioxoheptanoic acid in $CH_2Cl_2$ was added to 1 equiv. ethylenediamine in $CH_2Cl_2$ and the insoluble 1:1 condensation product immediately precipitated. The product was collected over a frit and dried in vacuo. The melting point was 140° C., with decomposition. A direct reaction of 4,6-dioxoheptanoic acid with monoacacen did not work, despite repeated attempts. Evidently, the acid group was effecting decomposition, even under anhydrous conditions. Nor did using excess triethylamine to neutralize the diketoacid give satisfactory results. "Acacaciden" (compound 13 in Scheme III): 1 equiv. aciden was powdered and Slurried in Fluka puriss. MeOH. 1 equiv. triethylamine and 2–2.5 equivalents acac were added and the mixture was allowed to stir overnight to give a yellow solution. It was evaporated to dryness to obtain the crude product as an orange oil. Further purification by flash chromatography over silica using a 5% to 25% gradient of MeOH in $Cl_2Cl_2$ with 0.5% TEA to guard against hydrolysis of imine bonds. Evaporation of solvent followed by recrystallization from EtOH gave a beige solid. M' was 282, as expected.

[Co(III)(acacen)($NH_3)_2$]Cl: Procedure obtained from Zvi Dori (The Technion, Haifa, Israel). 1 equiv. of acacen was degassed in vacuo and placed under argon. Dry, degassed methanol was transferred into the flask via cannula. 1 equiv. cobaltous acetate was treated in same manner and the resulting purple solution added via cannula to the clear solution of the ligand. An immediate color change from purple to orange was observed as the reaction was stirred under argon for two hours. Ammonia gas was bubbled into the solution and the flask opened to air. Reaction was stirred with ammonia for 4 hours, evaporating solvent replenished as necessary. The reddish solution was filtered over a frit and concentrated on a hot plate. Addition of saturated aqueous NaCl precipitates the brown product. It can be recrystallized from ethanol to give a tan powder.

[Co(III)(acacaciden)($NH_3)_2$]: The above metallation conditions were used, but with the acacaciden ligand. Crude reaction mixture did not afford precipitate, but purification over cation exchange resin using aqueous ammonium acetate followed by removal of the volatile buffer gave a light brown powder. M' was 373, as expected.

Peptide synthesis of GGGdFPR(SEQ ID NO: 1)amide: The peptides were synthesized by the Beckman Institute Biopolymer synthesis group (Caltech). This was accomplished on p-methylbenzhydrylamine (MBHA) resin using N-tert-butyloxycarbonyl (Boc) amino acid derivatives for Merrifield solid-phase synthesis on an A131 Model 430A peptide synthesizer. Tile terminal Boc protecting group was removed with trifluoroacetic acid (TFA). Side chain protecting groups and the peptide-resin bond were cleaved under HF conditions (90% HF, 5%p-cresol, 5%p-thiocresol). After removal of HF under vacuum, the peptide/resin mixture was washed on a fritted funnel with ether. The peptide was then dissolved in 10% aqueous acetic acid and filtered through. leaving the resin behind. The crude peptide solution was subjected to gel filtration on anion exchange resin AG 1-X2 to remove the scavengers. The peptide can be further purified by reversed-phase HPLC on a Vydac C8 column using a 30-min. linear gradient of 6–26% acctonitrile/water/0.1% TFA with a 2.0 mL/min. flow rate.

Coupled product [Co(III)(acacen-GGFPR)(NI$_3$)$_2$; (SEQ ID NO: 3) shown in FIG. 2]: One potential difficulty in coupling the cobalt complex to this peptide is that the peptide's arginine side chain is more reactive than its N-terminus if the arginine is not protected or protonated (Bodzansky, *Peptide Chemistry: A Practical Textbook*, Springer-Verlag, Berlin, 1988). Since arginine has a pK$_a$ around 12.0. it is easily protonated, but this renders the hydrophilic peptide insoluble in the organic solvents, such as dioxane, used for most coupling reactions. For this reason, we used the water-soluble coupling reagent 1-(3-dimethylamino-propyl)-3-ethylcarboiimide (EDC). At least a 10-fold excess of FDC is needed to compensate for its hydrolysis over the course of the reaction. The large quantity of urea byproduct generated can be reduced by passing the solution through an Amicon YC05 filter or by extracting the crude oil with an organic solvent.

In addition, HPLC purification of a basic, hydrophilic peptide usually calls for a small amount of an organic acid in the eluting solvent to aid retention. Since such an acid would attack the imine bonds of the free ligand, purification was attempted without it, but neither reverse phase C8 and C18 nor normal phase cyano columns were effective in resolving the mixture. Later, some progress was made using basic ammonium acetate buffer and acetonitrile on reversed phase, but there still was some decomposition of the product due to hydrolysis of the imine bonds. In order to prevent this, the imines were protected by inserting the metal into the ligand before attaching the peptide.

Synthesis was as follows. [CoIII(acacaciden)(NH$_3$)$_2$] was dissolved in 0.1 M HEPES buffer, pH 8 at 5° C. 1 equiv. peptide dissolved in the same buffer was added. 5 equiv. EDC were added directly. 4 hours later, another 5 equiv. were added. The reaction was stirred overnight at 5° C., then lyophilized to give a reddish brown product. The crude material was purified over cation exchange resin (Pharmacia G-25), eluting with ammonium acetate. Two products were collected, both of which contained the cobalt, based on reddish color, and the peptide, based on the presence of the phenylalaninie signals in the $^1$H NMR spectra (multiplets at 7.28 and 7.20 ppm). Mass spectrometry of both materials suggested that the first of the two to elute had lost an axial ligand, possibly replaced by coordination of the metal to arginine. This would likely deprotonate the arginine, lowering the overall charge to +1, causing it to elute earlier. Mass spectrometry also suggests that the second band contains the desired product, as the first had M$^+$=932, the second had M$^+$=1066. Tile calculated mass of the desired product as a diacetate salt is 1062.

Example 2

Inhibition of Carbonic Anhydrase

Inhibition of Co(III) compound

Bovine carbonic anhydrase (20 mg 6.7×10$^{-7}$ mol, Calbiochem) was dissolved in 0.5 mL Tris buffer (pH=8, 0.05 M). To this solution was added 30 mg of Co(II) hydroxypropyl acacen (30 mg, 7.6×10$^{-5}$ mol) dissolved in 0.5 mL of H$_2$O. This solution was incubated for 48 hours. The excess cobalt complex was separated from the protein using a PD-10 gel filtration column equilibrated with Tris buffer (pH 8, 0.05 M). This enzyme, which was incubated with the Co(III) complex, retained 100% of its activity.

Inhibition with Co(II) compound

Two samples of bovine carbonic anhydrase (30 mg, 1×10$^{-6}$ mol) were dissolved in 3 mL of degassed Tris buffer (pH 8, 0.05 M). To one of the samples was added Co(II) hydroxypropyl acacen (30 mg, 9×10$^{-5}$ mol). The other sample of bovine carbonic anhydrase served as the control. The solutions were incubated under inert atmosphere (glove box) and a 1 mL aliquot was removed from each sample after 48 and 96 hours of incubation. The protein was then exposed to air and the excess Co(II)hydroxypropyl acacen separated from the protein using a PD-10 gel filtration column (Pharmacia) equilibrated with Tris buffer (pH 8, 0.05 M). The enzymatic activity of the protein was assayed using p-nitroplhenylacetate as the substrate (Pocker et al., Biochem. 6:668–678 (1967)). The results are shown below:

| Inhibition of Carbonic Anhydrase (CA) with Co(II)hydroxypropyl acacen | |
|---|---|
| Time of incubation | % inhibition of CA |
| 48 hours | 33.8% |
| 96 hours | 43.2% |

Example 3

Inhibition of Thermolysin

Thermolysin (2,500,000 units, Calbiochem) was dissolved in 20 mL of Tris buffer (pH 7.2, 0.1 M, 2.5 M NaBr. 0.01 M CaCl$_2$) and stored at 4° C.; enzyme concentration was determined by using E$_{1\%}$$^{280}$=7.65 and a molecular weight of 34,600. This solution was further purified using gel filtration chromatography on an FPLC Using a Superdex 75 column (Pharmacia) equilibrated with 0.1 M Tris, 0.1 M NaBr, 0.01 CaCI, pH 7.2. This stock solution was stored at 4C. N-[3-(2-furyl)acryloyl]glycyl L-leuciniamide (FAGLA) was obtained from Sigma as the thermolysin substrate. A stock solution of FAGLA (4.0 mM) was prepared by dissolving the substrate in dimethylforthamide (DMF) and diluting it with buffer to a final concentration of 0.1 M Tris, 0.1 NaBr and 10 mM CaCl$_2$, pH 7.0 (final concentration of DMF was 2.5%; sec Feder et al., Biochem. 9:2784–2791 (1970)). For all assays, the concentration of enzyme and substrate was 50 nM and 2.0 mM respectively. The peptidase activity of thermolysin was determined by following the decrease in absorption at 346 due to the enzymatic hydrolysis of FAGLA. Initial velocities were determined for ≦10% of the reaction.

Thermolysin (2×10$^{-5}$ mol) was incubated with [Co(III) acacen(NH$_3$)$_2$]Cl (5 mM) in HEPES buffer (pH 7.0, 0.01 M, 0.005 M CaCl$_2$). The concentration of thermolysin was 5×10$^{-8}$ M, while the concentration of the cobalt inhibitor was $1.25 \times 10^{-5}$ M. The results of this study are shown below and in FIG. 3:

Inhibition of Thermolysin

| Time of incubation | % inhibition |
| --- | --- |
| 45 minutes | 46.2% |
| 190 minutes | 63.9% |
| 322 minutes | 77.7% |

Stock solution of thermolysin was mixed with the cobalt compound dissolved in 0.1 M Tris, 0.1 M NaBr, 0.01 $CaCl_2$, pH 7.2 (run buffer) to yield a final enzyme concentration of 10 mM and a cobalt concentration of 2.5 mM. These solutions were incubated at 25C or 37C for several hours along with a control lacking cobalt compound. Periodically 5 ml aliquots of these solutions were assayed for residual enzyme activity by their addition to a cuvette contain 495 mL of run buffer and 500 ml of FAGLA stock Solution, and following the absorption decrease at 346 nm as described above. All enzyme assays were performed at 25C. The results are shown in FIG. 3.

Ligand exchange experiments are shown in FIG. 3B. This experiment models the binding of the cobalt compounds to histidine residues on thermolysin by monitoring the binding of irnidazole to the bisamine product $(Co(III)acacen(NH_3)_2$ 1.35 mM of $Co(III)acacen(NH_3)_2$ was incubated with 0.1 M imidazole in run buffer. The rise in absorbance at 420 due to the exchange of $NH_3$ with imidazole was monitored with time at 25C and 37C. The similarity in the temperature dependence of enzyme inhibition and ligand exchange in the model cobalt complex suggests that ligand exchange with a histidine residue is the rate limiting step of enzyme inhibition.

The binding of the cobalt compound to the active site histidine was confirmed as follows. Thermolysin (10 $\mu$M in running buffer (0.1 M Tris, 0.1 M NaBr, 0.01 M $CaCl_2$, pH 7.2) was incubated at 25C with $Co(III)(acacen)(NH_3)_2Cl$ (5 mM) in the presence and absence of the inhibitor phosphoramidon (N-$\alpha$-L-rhamnopyransyloxyplhospho0-L-leucyl-L-tryptophan, 50 $\mu$M), which has a reported $K_1$ of 32 nM at pH 7.5 (Kitagishi et al., J. Biochem. 95:529–534 (1984). Phosphoramidon binds to thermolysin at the active site, and this enzyme-inhibitor complex has by crystallographically characterized (Weaver et al., J. Mol. Bio. 114:119–132 (1977)). After incubation with the cobalt compound overnight, the inhibitor was separated from the enzyme using gel filtration chromatography on an FPLC using a Superdex 75 column (Pharmacia) equilibrated with 0.1 M Tris, 5 mM $CaCl_2$, pH 9. The resulting solution was transferred into the Tris running buffer using a PD-10 column (Pharmacia), and was characterized. There was no detectable loss of enzyme activity due to irreversible inactivation by the cobalt complex after removal of the inhibitor. Spectrophotometric characterization of this active enzyme revealed the binding of two cobalt complexes to the enzyme. Characterization of thermolysin, completely inactivated by the cobalt complex, showed the binding of three equivalents of the cobalt compound for each enzyme molecule. Since protection of the active site prevents inhibitor of thermolysin, and it prevents the binding of one equivalent of cobalt compound to the enzyme, the inhibition of the enzyme is a consequence of the binding of one cobalt compound at the enzyme active site.

Example 4

Inhibition of Thrombin

Thrombin was chosen as the first target enzymic. Several crystal structures of thrombin are available from the Protein Data Bank (e.g. file 1PPB; see Bode et al., EMBO J. 8:3467 (1989)). Thrombin is a 34 kD scrine protease with a well defined mechanism of action involving a histidine residue. It is vital to the coagulation cascade, but an unwanted clot is a severe, life-threatening condition. Thrombin was chosen for this investigation because its structure and mechanism are well understood, there is a simple activity assay, and antithrombotic drugs are useful in the treatment of strokes.

Thrombin inhibition assay: As with any purified blood product, proper care was taken to avoid the transmission of blood-borne pathogens. Thrombin was taken as received (about 1 ml, at 30 $\mu$M in 0.75 M sodium chloride storage solution) and divided into 100 $\mu$L aliquots. Each aliquot was diluted to 10 ml. using clean. filtered (2 $\mu$m) aqueous 0.75 M NaCl and divided into 1 mL samples. Each sample was stored frozen at $-80°$ C. until ready for use. The protein should not be stored at $-20$ ° C. as this is too close to the cutectic point for the thrombin-salt mixture and freeze-thaw cycling may damage the protein.

An assay buffer containing 10 mM Tris, 10 mM HEPES, 0.1% polyethylene glycol (PEG 8000) and 500 mM sodium chloride was prepared to pH 8. Following manufacturer's instructions, 5 $\mu$mole Spectrozyme TH was dissolved in 1.000 mL filtered nanopure water. A series of $[Co^{III}(acacen)(NH_3)_2]Cl$ solutions was prepared by dissolving 16.6 mg of the compound in 0.75M NaCl and then diluting aliquots to a range of cobalt concentrations from 4.7 mM to 4.7 nM. Both of the purified materials were assayed.

Thrombin was preincubated with inhibitor in the kinetics buffer (total volume of thrombin, buffer, and inhibitor of 992 mL) for the times specified in FIG. 1. After incubation, the substrate, spectrozyme TH was added (8 mL of 5 mM spectrozyme), and the thrombin-catalyzed hydrolysis rates were monitored at 406 nm. The final concentration of thrombin in the experiments was 3 nM, and the concentration of substrate was 40 mM. The inhibitor concentrations are outlined in FIG. 1. The rates of hydrolysis were determined from the linear portion of the saturation-kinetics plots. The percent activity is determined by dividing the rate of spectrozyme hydrolysis with inhibitor by the rate of hydrolysis without inhibitor and multiplying by 100.

A vial of thrombin prepared as above was thawed in warm water. 100 $\mu$L aliquots were added to 100 $\mu$L, samples of the cobalt acacen solutions. One 100 $\mu$L aliquot of thrombin solution was diluted with 100 $\mu$L 0.75M NaCl to be used as a control. Samples were incubated as needed before assay. 980 $\mu$L of the assay buffer was placed in a 1.0 ml, 1 cm quartz cuvette and allowed to equilibrate to 25 ° C. (Hewett-Packard Peltier constant temperature cell holder). 10 $\mu$L of a sample was mixed thoroughly into the cell's contents. The spectrophotometer was set for a 30 second delay during which 10 $\mu$L. Spectrozyme TH solution was added and mixed into the cell's contents by inverting the capped cell a few times before replacing it in the spectrophotometer. Scans from 250 to 500 nm were taken every 30 seconds for 10 minutes, although a single-wavelength scan at 406 nm would suffice. After the runs, the control was allowed to hydrolyze to completion before determining the end point.

The absorbance values at 406 nm were extracted and used to find the pseudo-first order rate constant according to the formula:

$$ln[(A_\infty-A_t)/(A_\infty-A_o)]=kt$$

where $A_{28}$ is the absorbance at completion, $A_o$ is the initial absorbance (approximately the first data point) and $A_t$ is the absorbance at each time, t. The slope of the linear fit (typically $R^2>0.99$) yields k. Comparison to an uninhibited control sample gave an indication of the relative activity for each cobalt-containing sample. Controls were repeated periodically as a check for protein degradation.

First the inhibition of thrombin by unmodified [$Co^{III}$acacen)$NH_3$)$_2$]Cl was investigated. A solution containing 0.1 $\mu$M thrombin and 2.5 mM [$Co^{III}$(acaceni)($NH_3$)$_2$]Cl was incubated at room temperature for 24 hours. As a control, thrombin from the same source was incubated without inhibitor for the same length of time. A portion of each incubated solution was assayed at 25° C. with an excess of a commercial substrate, Spectrozyme TH, whose proteolysis releases a chromophore, p-nitroaniline. The pseudo-first order production of p-nitroaniline was monitored spectrophotometrically and the rate constant extracted for each run. The activity of the control sample was normal, but the cobalt-containing sample was completely inactive. The cobalt-free ligand had no effect.

The same experiment was set tip under an inert atmosphere, using a solution of water soluble Co(II) hydroxypropylacacen, at similar concentrations as before. After incubation, both sample and control were exposed to air to oxidize the cobalt. Again loss of activity was found for the cobalt-containing sample. Surprisingly, the Co(III) compound was a more effective inhibitor (0% activity) than the Co(II) compound (42% activity relative to its control). Perhaps the overall positive charge on the Co(III) compound assists in attracting the inhibitor to the active site as is seen in a different system (Bagger, J. Inorg. Biochem. 52:165 (1993)).

The [Co(III)acacen($NH_3$)$_2$]CI experiments were repeated for a range of cobalt concentrations from 2.4 mM to 2.4 nM after at 12 hour incubation at 25C. Cobalt concentrations as low as 24 $\mu$M were found to inhibit the protein. Incubation at a lower temperature. 5C, slows the onset of thrombin inhibition, just as it slows the ligand exchange of Co(III). Partial inhibition was observed over a range of cobalt concentrations after 3 hours at 5C. Activity was determined at 25C as before and was found to decrease with higher cobalt concentrations and longer incubation times. The activity of the control sample lacking the cobalt compound was stable over time. A crude attempt to determine the number of cobalt complexes bound to the enzyme was made by first passing the inhibited protein down a size exclusion column to remove most of the unbound cobalt complex and then determining the absorbance at two wavelengths for which the extinction coefficients of both pure thrombin and cobalt compound were known; this information gives the concentrations of each based on Beer's law. The initial estimate for two separate samples is 5–8 cobalts per enzyme. There are only five histidines in thrombin, but binding to other residues and electrostatic binding cannot be discounted.

Inhibition of Thrombin by Peptides Containing dPheProArg

The targeting approach requires attaching a recognition element to the cobalt complex for binding specifically to the active site of thrombin. The tripeptide sequence dPhe-Pro-Arg (dPhe or DFrehr to ** is a known inhibitor of thrombin, the arginine binding tightly to the PI aspartate. The peptides GGdFPR (SEQ ID NO: 4), GGGdFPR (SEQ ID NO: 1), GGFPR (SEQ ID NO: 3) and GGGIFPR (SEQ ID NO: 2)were obtained as amides and assayed against thrombin. As expected from the crystal structures and inhibition data for similar peptides, (Bajusz et al., Int. J. Peptide Protein Res. 12:217 (1978)), the dPhe-containing peptides were found to be better inhibitors since they can access a hydrophobic binding pocket more efficiently than the natural isomers. The $K_i$ for (Gly)$_3$dPhePioArg (SEQ ID NO: 2) is about 209 $\mu$M.

Both purified Co(III)-peptide compounds (the two peaks from cation exchange resin) were assayed against thrombin without additional purification, the concentrations of each determined by assuming that the extinction coefficients were similar to that of [$Co^{III}$(acacen)($NH_3$)$_2$]Cl (7,700 $M^{-1}cm^{-1}$). Preliminary results indicate that both inhibit at concentrations less than 1 $\mu$M, an order of magnitude lower than either [$Co^{III}$(acacen)($NH_3$)$_2$]Cl or the peptide alone.

Example 5

Inhibition of a Zinc Finger Transcription Factor

In order to demonstrate that cobalt compounds can disrupt the binding of a zinc finger to its consensus sequence, two model systems were used. Human Sp1 transcription factor, which contains three CCHH zinc fingers and a synthetic peptide representing the first zinc finger region of retroviral nucleocapsid protein.

Inhibition of Sp1 Binding

Samples containing 20 ul of binding buffer (25 mM Tris pH 8.0, 100 mM KCl, 2 mM DTT, 100 uM ZnCl2, 10% glycerol) and 25 ng of Sp1 (Promega) were incubated with 40 fmol of 32P labeled oligonucleotide in the presence or absence of cobalt chelate complex (Co(III)acacen with either $NH_3$ or imidazole as the axial ligands) at various concentrations (0.001 to 0.05 mM) and evaluated by gel shift and filter binding assays.

Gel shift: Samples were run on a 4% polyacrylamide gel (80:1 ) at room temperature, 100V, in 0.5 X TBE. Gels had been prerun for 30 minutes prior to loading. These experiments demonstrated that the presence of cobalt complex inhibited the binding of Sp1 to consensus oligonucleotide.

Filter Binding Assay: The above samples were applied to nitrocellulose (0.45 um filters, Schlcicher and Schuell) and washed twice with washing buffer (100 mM HEPES, pH 7.5, 1 mM ETDA). Membranes were incubated for 15 minutes at room temperature with Filtron-X (National Diagnostics) and bound Counts were detected by liquid scintillation (Beckman Instruments). Increasing amounts of cobalt compound resulted in decreased counts bound to the filter, indicating a loss of binding between Sp1 and oligonucleotide.

Disruption of the Structure of a Synthetic Retroviral Zinc Finger

An 18 amino acid peptide corresponding to the first zinc finger region of the HIV nucleocapsid protein was synthesized and examined in a series of structural studies.

Confirmation of Zinc Finger Structure: 0.1 mg .ml solutions of peptide in 25 mM phosphate buffer pH 7.0 were examined by circular dichroism spectroscopy. In the absence of zinc, peptides displayed spectra characteristic of random coil structure. In the presence of zinc, the spectra changed dramatically to one indicative of type 11 turn content and zinc finger structure.

Disruption of Zinc Finger Structure: 4 mg peptide in 350 ul $D_2O$ was subjected to protein NMR spectroscopy. Spectra in the absence of zinc displayed multiple peaks in the aromatic region, including peaks representing protons from metal-free histidine. In the presence of zinc those peaks disappeared and were replaced by peaks representing protons from metal-bound histidine. The presence of cobalt compound resulted in a dramatically altered spectra indicating disturbance of the structure of the peptide.

We claim:
1. A compound having the formula comprising:

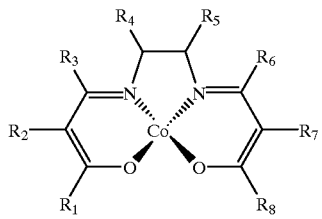

wherein
Co is either Co(II) or Co(III);
R$_1$ is hydrogen, alkyl, hydrophilic organic acid, alkyl amine, amine, alkyl alcohol, alcohol, aryl polypeptide or nucleic acid;
R$_2$ is hydrogen, alkyl, hydrophilic organic acid, alkyl amine, amine, alkyl alcohol, alcohol, aryl polypeptide or nucleic acid;
R$_3$ is hydrogen, alkyl, hydrophilic organic acid, alkyl amine, amine, alkyl alcohol, alcohol, aryl polypeptide or nucleic acid;
R$_4$ is hydrogen, alkyl, hydrophilic organic acid, alkyl amine, amine, alkyl alcohol, alcohol, aryl polypeptide or nucleic acid;
R$_5$ is hydrogen, alkyl, hydrophilic organic acid, alkyl amine, amine, alkyl alcohol, alcohol, aryl polypeptide or nucleic acid;
R6 is hydrogen, alkyl, hydrophilic organic acid, alkyl amine, amine, alkyl alcohol, alcohol, aryl polypeptide or nucleic acid;
R$_7$ is hydrogen, alkyl, hydrophilic organic acid, alkyl amine, amine, alkyl alcohol, alcohol, aryl, polypeptide or nucleic acid; and
R$_8$ is hydrogen, alkyl, hydrophilic organic acid, alkyl amine, amine, alkyl alcohol, alcohol, aryl, polypeptide or nucleic acid;
wherein at least one of R$_1$, R$_2$, R$_3$, R$_4$, R$_5$, R, R$_7$ and R$_8$ is either a polypeptide or a nucleic acid.

2. A compound according to claim 1 wherein Co is Co(II).
3. A compound according to claim 1 wherein Co is Co(III).
4. A compound according to claim 1 wherein R$_1$, R$_2$, R$_3$, and R$_4$ are each hydrogen, alkyl or aryl.
5. A compound according to claim 1 further comprises a first axial ligand.
6. A protein-cobalt compound complex comprising a protein and a cobalt compound attached thereto wherein said cobalt compound has the structure shown in claim 1.
7. A complex according to claim 6 wherein said protein is an enzyme.
8. A method of inhibiting a target protein comprising contacting said target protein with the compound of claim 1.
9. A method according to claim 8 wherein said protein is an enzyme.

10. A method of inhibiting a zinc finger protein comprising contacting a zinc finger protein with a compound having the structure comprising:

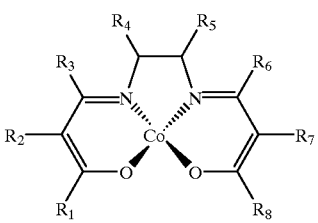

wherein
Co is either Co(II) or Co(III);
R$_1$ is hydrogen, alkyl, aryl, hydrophilic organic acid, alkyl amine, amine, alkyl alcohol, alcohol, polypeptide or nucleic acid;
R$_2$ is hydrogen, alkyl, aryl, hydrophilic organic acid, alkyl amine, amine, alkyl alcohol, alcohol, polypeptide or nucleic acid;
R$_3$ is hydrogen, alkyl, aryl, hydrophilic organic acid, alkyl amine, amine, alkyl alcohol, alcohol, polypeptide or nucleic acid;
R$_4$ is hydrogen, alkyl, aryl, hydrophilic organic acid, alkyl amine, amine, alkyl alcohol, alcohol, polypeptide or nucleic acid;
R$_5$ is hydrogen, alkyl, aryl, hydrophilic organic acid, alkyl amine, amine, alkyl alcohol, alcohol, polypeptide or nucleic acid;
R$_6$ is hydrogen, alkyl, aryl, hydrophilic organic acid, alkyl amine, amine, alkyl alcohol, alcohol, polypeptide or nucleic acid;
R$_7$ is hydrogen, alkyl, aryl, hydrophilic organic acid, alkyl amine, amine, alkyl alcohol, alcohol, polypeptide or nucleic acid; and
R$_8$ is hydrogen, alkyl, aryl, hydrophilic organic acid, alkyl amine, amine, alkyl alcohol, alcohol, polypeptide or nucleic acid.

11. A method according to claim 10 wherein R$_1$ is N-hydroxypropyl, R$_2$ is hydrogen, R$_3$ is methyl, R$_6$ is methyl, R$_7$ is hydrogen, R8 is methyl, and R$_4$ and R$_5$ are hydrogen.
12. A complex according to claim 6 wherein said protein is a zinc-finger protein.
13. A complex according to claim 7 wherein said enzyme is a protease.
14. A complex according to claim 13 wherein said protease is selected from the group consisting of serine proteases and cysteine proteases.
15. A method according to claim 8 wherein said protein is a zinc-finger protein.
16. A method according to claim 9 wherein said enzyme is a protease.

17. A method according to claim 16 wherein said protease is selected from the group consisting of serine proteases and cysteine proteases.

18. A method according to claim 10 wherein at least one of $R_1$, $R_2$, $R_3$, $R_4$, $R_5$, $R_6$, $R_7$, and $R_8$ is a polypeptide or nucleic acid.

19. A method according to claim 10 wherein at least one of $R_1$, $R_2$, $R_3$, $R_4$, $R_5$, $R_6$, $R_7$, and $R_8$ is a nucleic acid.

20. A method according to claim 10 wherein Co is Co(II).

21. A method according to claim 10 wherein Co is Co(III).

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: unknown
      (D) TOPOLOGY: unknown (ii) MOLECULE TYPE: protein (ix) FEATURE:
      (A) NAME/KEY: Modified-site
      (B) LOCATION: 4..5
      (D) OTHER INFORMATION: /note= "The X at position 4
         represents "dF" or D-phenylalanine."

(xi) SEQUENCE DESCRIPTION: SEQ ID NO:1:

Gly Gly Gly Xaa Pro Arg
1               5

(2) INFORMATION FOR SEQ ID NO:2:

(i) SEQUENCE CHARACTERISTICS:
      (A) LENGTH: 6 amino acids
      (B) TYPE: amino acid
      (C) STRANDEDNESS: unknown
      (D) TOPOLOGY: unknown (ii) MOLECULE TYPE: protein (xi) SEQUENCE DESCRIPTION: SEQ ID NO:2:

Gly Gly Gly Phe Pro Arg
1               5

(2) INFORMATION FOR SEQ ID NO:3:

(i) SEQUENCE CHARACTERISTICS:
      (A) LENGTH: 5 amino acids
      (B) TYPE: amino acid
      (C) STRANDEDNESS: unknown
      (D) TOPOLOGY: unknown (ii) MOLECULE TYPE: protein (xi) SEQUENCE DESCRIPTION: SEQ ID NO:3:

Gly Gly Phe Pro Arg
1               5

(2) INFORMATION FOR SEQ ID NO:4:

(i) SEQUENCE CHARACTERISTICS:
      (A) LENGTH: 5 amino acids
      (B) TYPE: amino acid
      (C) STRANDEDNESS: unknown
      (D) TOPOLOGY: unknown (ii) MOLECULE TYPE: protein (ix) FEATURE:
      (A) NAME/KEY: Modified-site
      (B) LOCATION: 3..4
      (D) OTHER INFORMATION: /note= "The 'X' at position 3
         represents 'dF' or D-phenylalanine."

(xi) SEQUENCE DESCRIPTION: SEQ ID NO:4:

Gly Gly Xaa Pro Arg
1               5